US007588577B2

(12) United States Patent
Fencl et al.

(10) Patent No.: US 7,588,577 B2
(45) Date of Patent: Sep. 15, 2009

(54) GUIDE ASSEMBLY FOR INTRAMEDULLARY FIXATION AND METHOD OF USING THE SAME

(75) Inventors: Robert M. Fencl, Cordova, TN (US); Mark J. Warburton, High Point, NC (US); John T. Capo, Hoboken, NJ (US); Virak Tan, Murray Hill, NJ (US); Aaron C. Smith, Arlington, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 761 days.

(21) Appl. No.: 10/891,738

(22) Filed: Jul. 15, 2004

(65) Prior Publication Data

US 2006/0015123 A1 Jan. 19, 2006

(51) Int. Cl.
*A61B 17/58* (2006.01)
*A61B 17/60* (2006.01)
*A61F 2/00* (2006.01)

(52) U.S. Cl. .............................. 606/96; 606/62; 606/87; 606/104

(58) Field of Classification Search ................... 606/62, 606/64, 86, 96–99, 63, 65–68; 403/13, 14
See application file for complete search history.

(56) References Cited

U.S. PATENT DOCUMENTS

| 2,500,370 A | 3/1950 | McKibbin |
|---|---|---|
| 2,682,265 A | 6/1954 | Collison |
| 3,334,624 A | 8/1967 | Schneider et al. |
| 3,433,220 A | 3/1969 | Zickel |
| 3,709,218 A | 1/1973 | Halloran |
| 3,939,498 A | 2/1976 | Lee et al. |
| 3,973,278 A | 8/1976 | Shersher |

(Continued)

FOREIGN PATENT DOCUMENTS

DE 7 115 713 6/1975

(Continued)

OTHER PUBLICATIONS

International Search Report for PCT/US2005/025059, mailed Feb. 14, 2006.

(Continued)

*Primary Examiner*—Thomas C Barrett
*Assistant Examiner*—Andrew Yang
(74) *Attorney, Agent, or Firm*—Alston & Bird LLP

(57) ABSTRACT

An intramedullary fixation assembly usable with different long bone types and a guide assembly for guiding deployment of the intramedullary fixation assembly. The intramedullary fixation assembly includes a fixation member that has ends and a curved body extending between the ends. The curved body of the fixation member has a radius of curvature configured to extend through the medullary canal regardless of the long bone anatomy. Fasteners fix the fixation member to the bone fragments and are guided by a guide assembly. The guide assembly includes a guide body defining openings configured to guide the fasteners through openings defined in the fixation member and into the bone fragments. A fixation end of the guide body includes a pair of opposing, converging surfaces that are configured to engage in a positive fit with an exposed end of the fixation member accessible through the side aperture in the first fragment.

42 Claims, 38 Drawing Sheets

U.S. PATENT DOCUMENTS

| | | |
|---|---|---|
| 3,977,398 A | 8/1976 | Burstein |
| 4,011,863 A | 3/1977 | Zickel |
| 4,055,172 A | 10/1977 | Ender et al. |
| 4,091,806 A | 5/1978 | Aginsky |
| 4,103,683 A | 8/1978 | Neufeld |
| 4,135,507 A | 1/1979 | Harris |
| 4,169,470 A | 10/1979 | Ender et al. |
| 4,227,518 A | 10/1980 | Aginsky |
| 4,237,875 A | 12/1980 | Termanini |
| 4,274,754 A * | 6/1981 | Cohen .................. 403/14 |
| 4,338,926 A | 7/1982 | Kummer |
| 4,393,868 A | 7/1983 | Teague |
| 4,423,721 A | 1/1984 | Otte et al. |
| 4,446,857 A | 5/1984 | Otte et al. |
| 4,453,539 A | 6/1984 | Raftopoulos et al. |
| 4,467,793 A | 8/1984 | Ender |
| 4,473,069 A | 9/1984 | Kolmert |
| 4,475,545 A | 10/1984 | Ender |
| 4,483,335 A | 11/1984 | Tornier |
| 4,493,317 A | 1/1985 | Klaue |
| 4,513,744 A | 4/1985 | Klaue |
| 4,522,202 A | 6/1985 | Otte et al. |
| 4,541,424 A | 9/1985 | Grosse et al. |
| 4,590,930 A | 5/1986 | Kurth et al. |
| 4,622,959 A * | 11/1986 | Marcus .................. 606/64 |
| 4,630,601 A | 12/1986 | Harder et al. |
| 4,667,663 A | 5/1987 | Miyata |
| 4,697,585 A | 10/1987 | Williams |
| 4,705,027 A | 11/1987 | Klaue |
| 4,712,541 A | 12/1987 | Harder et al. |
| 4,733,654 A | 3/1988 | Marino |
| 4,775,381 A | 10/1988 | Tari et al. |
| 4,781,181 A | 11/1988 | Tanguy |
| 4,794,919 A | 1/1989 | Nilsson |
| 4,805,607 A | 2/1989 | Engelhardt et al. |
| 4,846,162 A | 7/1989 | Moehring |
| 4,854,312 A | 8/1989 | Raftopoulos et al. |
| 4,858,602 A | 8/1989 | Seidel et al. |
| 4,875,474 A | 10/1989 | Border |
| 4,877,019 A | 10/1989 | Vives |
| 4,911,153 A | 3/1990 | Border |
| 4,943,291 A | 7/1990 | Tanguy |
| 4,944,764 A | 7/1990 | Stossel |
| 4,946,459 A | 8/1990 | Bradshaw et al. |
| 4,976,258 A | 12/1990 | Richter et al. |
| 4,976,714 A | 12/1990 | Aghion |
| 5,013,314 A | 5/1991 | Firica et al. |
| 5,035,697 A | 7/1991 | Frigg |
| 5,041,115 A | 8/1991 | Frigg et al. |
| 5,057,103 A | 10/1991 | Davis |
| 5,057,110 A | 10/1991 | Kranz et al. |
| 5,066,296 A | 11/1991 | Chapman et al. |
| 5,084,053 A | 1/1992 | Ender |
| 5,100,404 A | 3/1992 | Hayes |
| 5,122,146 A | 6/1992 | Chapman et al. |
| 5,135,527 A | 8/1992 | Ender |
| 5,167,666 A | 12/1992 | Mattheck et al. |
| 5,190,543 A | 3/1993 | Schlapfer |
| 5,197,966 A | 3/1993 | Sommerkamp |
| 5,201,735 A | 4/1993 | Chapman et al. |
| 5,211,645 A | 5/1993 | Baumgart et al. |
| 5,239,569 A | 8/1993 | Saleh et al. |
| 5,248,313 A | 9/1993 | Greene et al. |
| 5,263,955 A | 11/1993 | Baumgart et al. |
| 5,268,000 A | 12/1993 | Ottieri et al. |
| 5,281,224 A | 1/1994 | Faccioli et al. |
| 5,295,991 A | 3/1994 | Frigg |
| 5,334,192 A | 8/1994 | Behrens |
| 5,352,228 A | 10/1994 | Kummer et al. |
| 5,356,410 A | 10/1994 | Pennig |
| 5,397,328 A | 3/1995 | Behrens et al. |
| 5,411,503 A | 5/1995 | Hollstien et al. |
| 5,415,660 A | 5/1995 | Campbell et al. |
| 5,429,638 A | 7/1995 | Muschler et al. |
| 5,433,718 A | 7/1995 | Brinker |
| 5,441,500 A | 8/1995 | Seidel et al. |
| 5,443,466 A | 8/1995 | Shah |
| 5,458,654 A | 10/1995 | Tepic |
| 5,472,444 A | 12/1995 | Huebner et al. |
| 5,484,438 A | 1/1996 | Pennig |
| 5,499,986 A | 3/1996 | Dimarco |
| 5,536,269 A | 7/1996 | Spievack |
| 5,549,610 A | 8/1996 | Russell et al. |
| 5,569,262 A | 10/1996 | Carney |
| 5,573,536 A | 11/1996 | Grosse et al. |
| 5,578,035 A | 11/1996 | Lin |
| 5,586,985 A | 12/1996 | Putnam et al. |
| 5,618,286 A | 4/1997 | Brinker |
| 5,620,445 A | 4/1997 | Brosnahan et al. |
| 5,620,449 A | 4/1997 | Faccioli et al. |
| 5,626,579 A | 5/1997 | Muschler et al. |
| 5,643,258 A | 7/1997 | Robioneck et al. |
| 5,645,545 A | 7/1997 | Bryant |
| 5,653,709 A | 8/1997 | Frigg |
| 5,658,283 A | 8/1997 | Huebner |
| 5,658,287 A | 8/1997 | Hofmann et al. |
| 5,665,086 A | 9/1997 | Itoman et al. |
| 5,681,318 A | 10/1997 | Pennig et al. |
| 5,690,634 A | 11/1997 | Muller et al. |
| 5,697,930 A | 12/1997 | Itoman et al. |
| 5,697,934 A | 12/1997 | Heubner |
| 5,713,902 A | 2/1998 | Friedl |
| 5,718,704 A | 2/1998 | Medoff |
| 5,728,128 A * | 3/1998 | Crickenberger et al. ....... 606/97 |
| 5,766,174 A * | 6/1998 | Perry .................. 606/62 |
| 5,766,179 A * | 6/1998 | Faccioli et al. .................. 606/98 |
| 5,766,180 A | 6/1998 | Winquist |
| 5,776,194 A | 7/1998 | Mikol et al. |
| 5,779,705 A | 7/1998 | Matthews |
| 5,853,413 A | 12/1998 | Carter et al. |
| 5,928,235 A | 7/1999 | Friedl |
| 5,941,878 A | 8/1999 | Medoff |
| 5,954,722 A | 9/1999 | Bono |
| 5,961,553 A | 10/1999 | Coty et al. |
| 5,976,134 A | 11/1999 | Huebner |
| 5,997,490 A | 12/1999 | McLeod et al. |
| 6,010,505 A | 1/2000 | Asche et al. |
| 6,010,506 A | 1/2000 | Gosney et al. |
| 6,019,761 A | 2/2000 | Gustilo |
| 6,022,349 A | 2/2000 | McLeod et al. |
| 6,027,506 A | 2/2000 | Faccioli et al. |
| 6,033,407 A | 3/2000 | Behrens |
| 6,056,755 A | 5/2000 | Horas et al. |
| 6,074,392 A | 6/2000 | Durham |
| 6,077,264 A | 6/2000 | Chemello |
| 6,080,159 A | 6/2000 | Vichard |
| 6,093,192 A | 7/2000 | Abel |
| 6,096,040 A | 8/2000 | Esser |
| 6,120,504 A | 9/2000 | Brumback et al. |
| 6,123,708 A | 9/2000 | Kilpela et al. |
| 6,123,709 A | 9/2000 | Jones |
| 6,126,661 A | 10/2000 | Faccioli et al. |
| 6,146,384 A | 11/2000 | Lee et al. |
| 6,168,628 B1 * | 1/2001 | Huebner .................. 623/19.11 |
| 6,200,321 B1 | 3/2001 | Orbay et al. |
| 6,206,880 B1 | 3/2001 | Karladani |
| 6,221,073 B1 | 4/2001 | Weiss et al. |
| 6,221,074 B1 | 4/2001 | Cole et al. |
| 6,224,601 B1 | 5/2001 | Friedl |
| 6,228,086 B1 | 5/2001 | Wahl et al. |
| 6,231,576 B1 | 5/2001 | Frigg et al. |
| 6,245,075 B1 | 6/2001 | Betz et al. |
| 6,248,109 B1 | 6/2001 | Stoffella |
| 6,261,289 B1 | 7/2001 | Levy |

| | | |
|---|---|---|
| 6,270,499 B1 | 8/2001 | Leu et al. |
| 6,273,892 B1 | 8/2001 | Orbay et al. |
| 6,283,969 B1 | 9/2001 | Grusin et al. |
| 6,296,645 B1 | 10/2001 | Hover et al. |
| 6,319,253 B1 | 11/2001 | Ackeret et al. |
| 6,358,250 B1 | 3/2002 | Orbay |
| 6,364,882 B1 | 4/2002 | Orbay |
| 6,379,359 B1 | 4/2002 | Dahners |
| 6,379,360 B1 | 4/2002 | Ackeret et al. |
| 6,383,185 B1 | 5/2002 | Baumgart |
| 6,387,098 B1 | 5/2002 | Cole et al. |
| 6,395,033 B1 | 5/2002 | Pepper |
| 6,402,753 B1 | 6/2002 | Cole et al. |
| 6,409,768 B1 | 6/2002 | Tepic et al. |
| 6,416,516 B1 | 7/2002 | Stauch et al. |
| 6,423,066 B1 | 7/2002 | Harder et al. |
| 6,440,135 B2 | 8/2002 | Orbay et al. |
| 6,443,954 B1 | 9/2002 | Bramlet et al. |
| 6,461,360 B1 | 10/2002 | Adam |
| 6,488,684 B2 | 12/2002 | Bramlet et al. |
| 6,508,819 B1 | 1/2003 | Orbay |
| 6,508,820 B2 | 1/2003 | Bales |
| 6,514,253 B1 | 2/2003 | Yao |
| 6,524,313 B1 | 2/2003 | Fassir et al. |
| 6,524,314 B1 | 2/2003 | Dean et al. |
| 6,527,775 B1 | 3/2003 | Warburton |
| 6,533,788 B1 | 3/2003 | Orbay |
| 6,547,791 B1 | 4/2003 | Buhren et al. |
| 6,554,833 B2 | 4/2003 | Levy et al. |
| 6,572,620 B1 | 6/2003 | Schon et al. |
| 6,579,294 B2 | 6/2003 | Robioneck |
| 6,607,531 B2 | 8/2003 | Frigg |
| 6,629,976 B1 | 10/2003 | Gnos et al. |
| 6,648,889 B2 | 11/2003 | Bramlet et al. |
| 6,652,529 B2 | 11/2003 | Swanson |
| 6,658,189 B2 | 12/2003 | Ajima et al. |
| 6,660,009 B1 | 12/2003 | Azar |
| 6,702,823 B2 | 3/2004 | Iaia |
| 6,706,046 B2 * | 3/2004 | Orbay et al. ............ 606/69 |
| 6,709,436 B1 | 3/2004 | Hover et al. |
| 6,730,087 B1 | 5/2004 | Butsch |
| 6,730,090 B2 | 5/2004 | Orbay et al. |
| 6,736,818 B2 | 5/2004 | Perren et al. |
| 6,755,862 B2 | 6/2004 | Keynan |
| 6,767,351 B2 | 7/2004 | Orbay et al. |
| 6,786,908 B2 | 9/2004 | Hover et al. |
| 6,793,659 B2 | 9/2004 | Putnam |
| 6,796,984 B2 | 9/2004 | Soubeiran |
| 6,808,527 B2 | 10/2004 | Lower et al. |
| 6,866,665 B2 | 3/2005 | Orbay |
| 6,893,444 B2 | 5/2005 | Orbay |
| 6,926,720 B2 * | 8/2005 | Castaneda ............ 606/98 |
| 7,018,380 B2 | 3/2006 | Cole |
| 7,033,365 B2 | 4/2006 | Powell et al. |
| 7,041,104 B1 | 5/2006 | Cole et al. |
| 7,175,633 B2 * | 2/2007 | Roth et al. ............ 606/99 |
| 2001/0011172 A1 | 8/2001 | Orbay et al. |
| 2002/0032446 A1 | 3/2002 | Orbay |
| 2002/0111629 A1 | 8/2002 | Phillips |
| 2002/0143337 A1 | 10/2002 | Orbay et al. |
| 2002/0143338 A1 | 10/2002 | Orbay et al. |
| 2002/0151897 A1 * | 10/2002 | Zirkle, Jr. ............ 606/62 |
| 2002/0183753 A1 | 12/2002 | Manderson |
| 2003/0055428 A1 | 3/2003 | Swanson |
| 2003/0069581 A1 | 4/2003 | Stinson et al. |
| 2003/0073999 A1 | 4/2003 | Putnam |
| 2003/0083660 A1 | 5/2003 | Orbay |
| 2003/0083661 A1 | 5/2003 | Orbay et al. |
| 2003/0105461 A1 | 6/2003 | Putnam |
| 2004/0082955 A1 | 4/2004 | Zirkle, Jr. |
| 2004/0172026 A1 | 9/2004 | Ekholm et al. |
| 2006/0200143 A1 | 9/2006 | Warburton |
| 2006/0200144 A1 | 9/2006 | Warburton |

FOREIGN PATENT DOCUMENTS

| | | |
|---|---|---|
| DE | 8 533 134.1 | 11/1985 |
| EP | 0 091 499 A1 | 10/1983 |
| EP | 0 118 778 | 9/1984 |
| EP | 0 355 411 | 7/1989 |
| EP | 0 491 138 B1 | 10/1991 |
| EP | 0 649 289 B1 | 5/1992 |
| EP | 1 095 626 | 4/2000 |
| FR | 2 586 554 | 8/1985 |
| FR | 2 668 360 | 10/1990 |
| GB | 1 428 653 | 3/1976 |
| JP | 2 274 243 | 8/1990 |
| WO | WO-98/18397 | 5/1998 |
| WO | WO 01/56452 A2 | 1/2001 |
| WO | WO 01/56452 A3 | 1/2001 |
| WO | WO 03/037160 A2 | 10/2002 |

OTHER PUBLICATIONS

Written Opinion for PCT/US2005/025059, mailed Feb. 14, 2006.
"The Next Generation in Nail Fixation: Symposium: Current Concepts in Femoral Nailing," vol. 26(2) (1993), 35 pages.
"The Alta Tibial/Humeral Rod Module for Reamed and Non-Reamed Procedures," Alta Modular Trauma System, (1992), 10 pages.
"Proximal Humeral Nailing System: Operative Technique," Stryker Corporation (2003), 20 pages.
"Intramedullary Fixation: Metaphysical/Diaphyseal Solutions," Zimmer, 6 pages (2000).
"Uniflex Humeral Nail System," Biomet Inc. (1991), 16 pages.
"RAL Nail System: Titanium for Your Most Demanding Cases," ACUMED 00674, 13 pages.
Richard S. Smith, John C. Crick, Jorge Alonso, Marshall Horowitz, Open Reduction and Internal Fixation of Volar Lip Fractures of the Distal Radius, *Journal of Orthopaedic Trauma*, 1988, pp. 181-187, vol. 2 No. 3, Raven Press, Ltd., New York.
Jorge L. Orbay, Diego L. Fernandez, Volar Fixation for Dorsally Displaced Fractures of the Distal Radius: A Preliminary Report, *The Journal of Hand Surgery*, 2002, pp. 205-215, Miami, Florida.
Jorge L. Orbay, The Treatment of Unstable Distal Radius Fractures with Volar Fixation, *Hand Surgery*, Dec. 2000, pp. 103-112, vol. 5 No. 2, World Scientific Publishing Company.
Charles P. Melone, Jr., MD, Distal Radius Fractures: Patterns of Articular Fragmentation, *Orthopedic Clinics of North America*, Apr. 1993, pp. 239-253, vol. 24 No. 2.
Smith's Type I Fracture, *Fractures of the Hand & Wrist*, p. 254.
F. Fitoussi, W.Y. IP, S.P. Chow, Treatment of Displaced Intra-Articular Fractures of the Distal End of the Radius with Plates Article, *JBJA Journal of Bone and Joint Surgery—American 1996-1998*, Sep. 1997, 17 pgs., vol. 79-A, No. 9.
H. Drobetz, E. Kutscha-Lissberg, Osteosynthesis of distal radial fractures with a volar locking screw plate system, *International Orthopaedics*, Aug. 21, 2002, pp. 1-6, Springer-Verlag 2002.
Timothy A. Damron, MD, Peter J.L. Jebson, MD, Venkat K. Rao, MD, William D. Engber, MD, Mark A Norden, BS, Biomechanical Analysis of Dorsal Plate Fixation in Proximal Phalangeal Fractures, *Annals of Plastic Surgery*, Apr. 2, 1993, pp. 270-275, Little, Brown & Company.

* cited by examiner

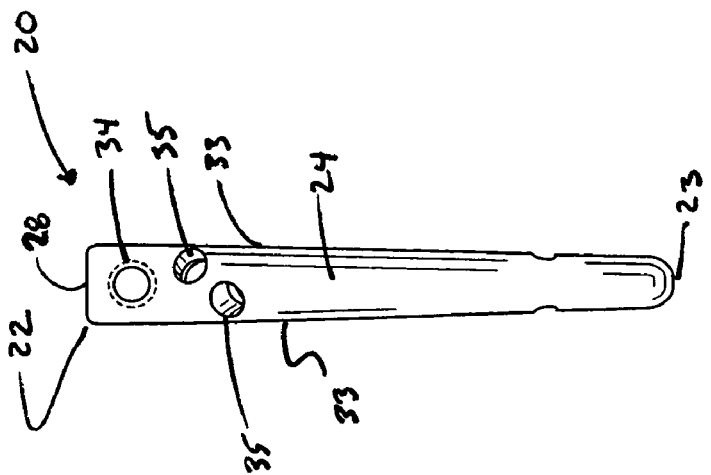
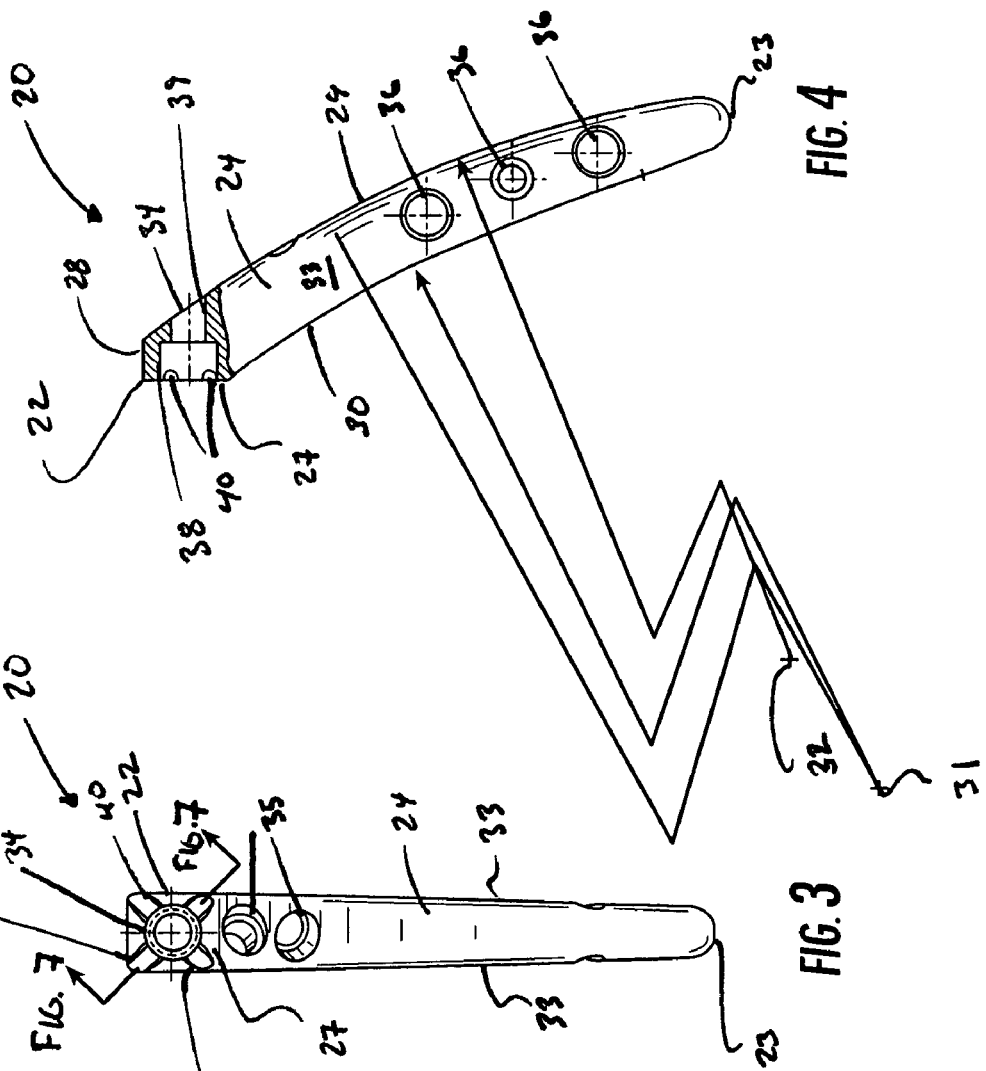
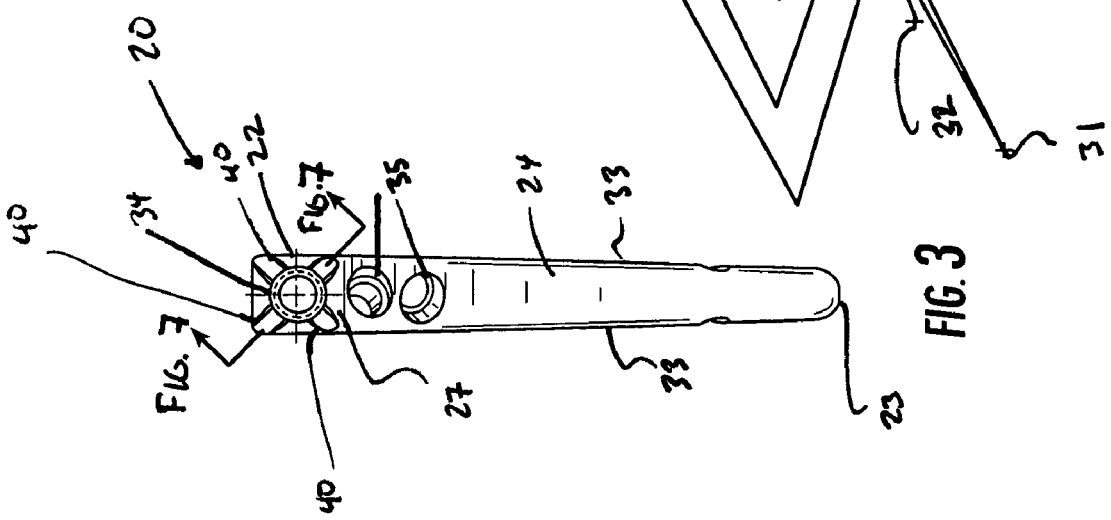

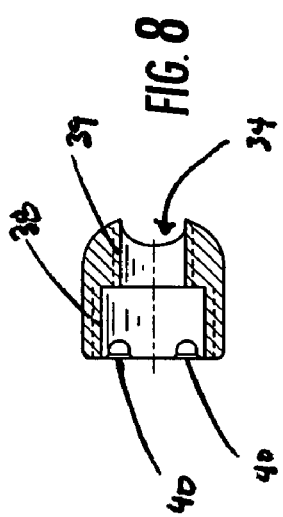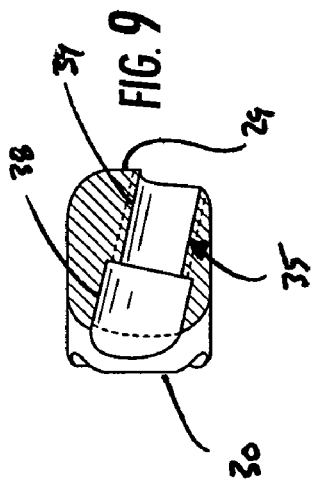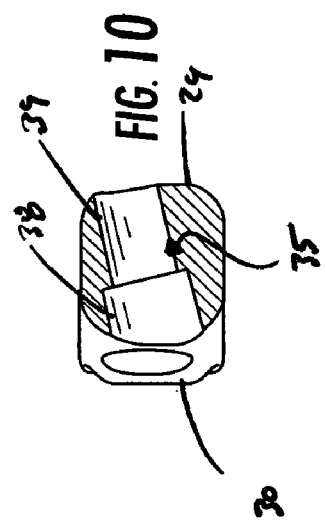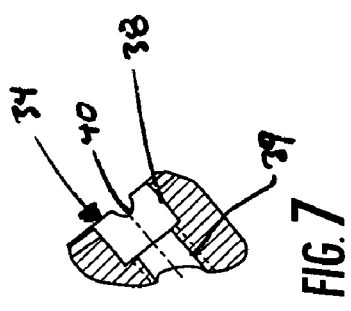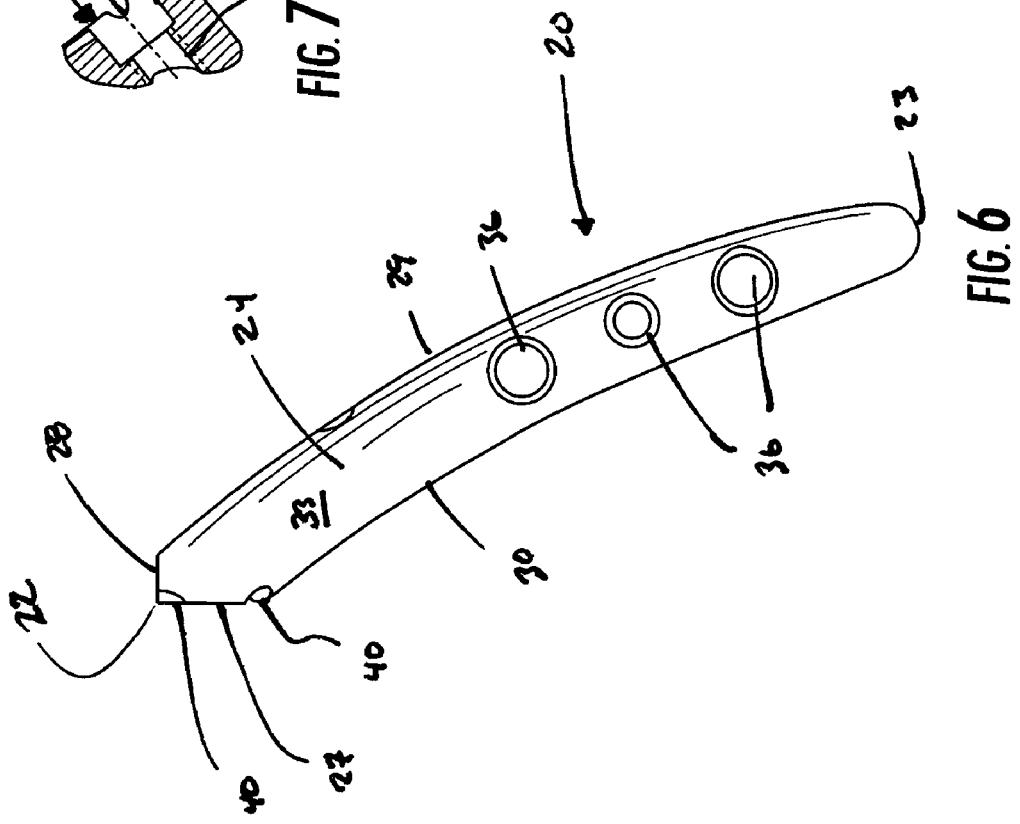

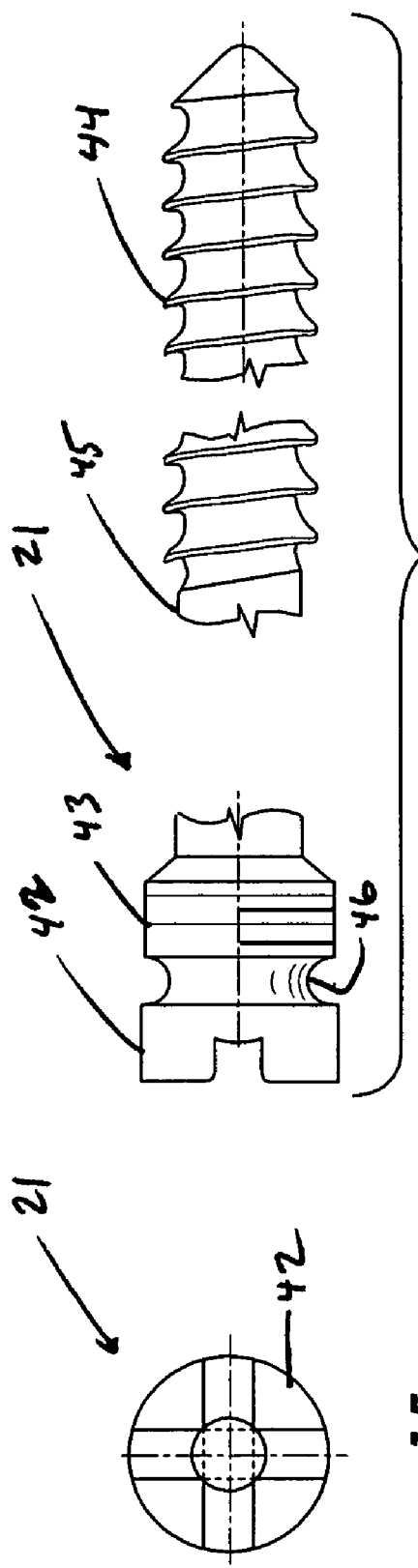

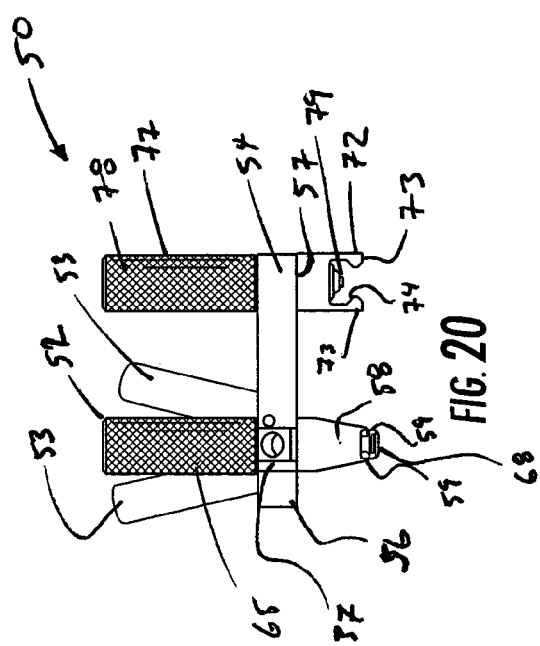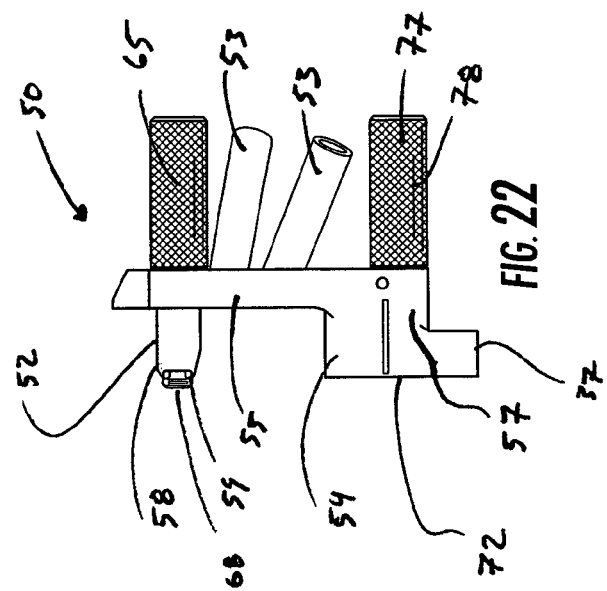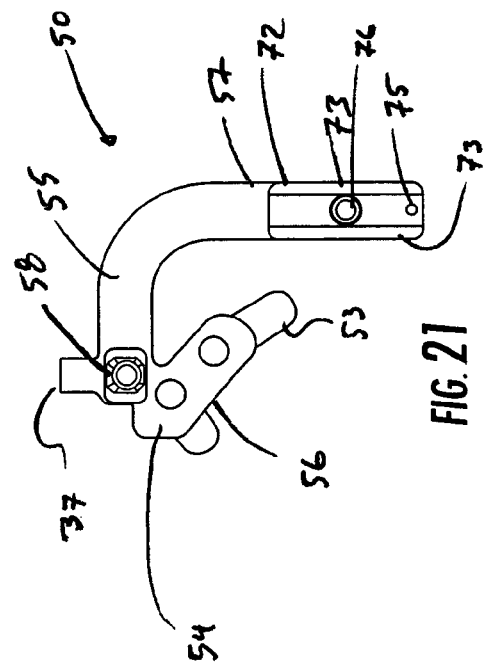

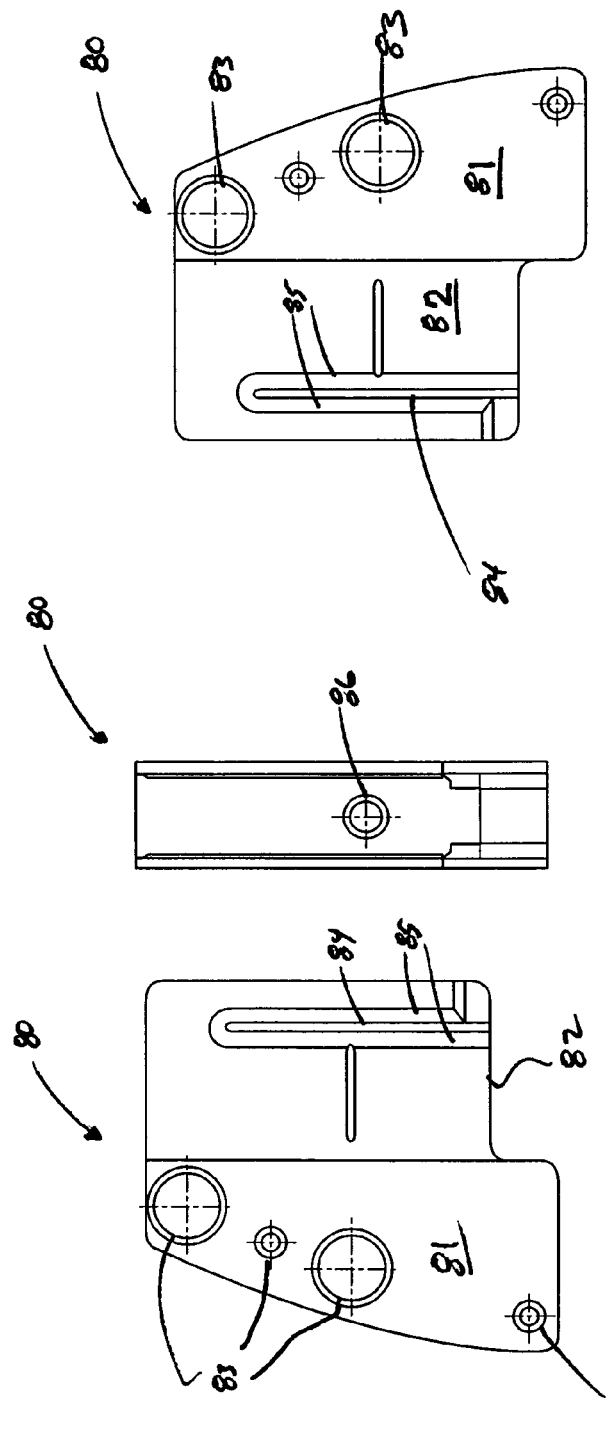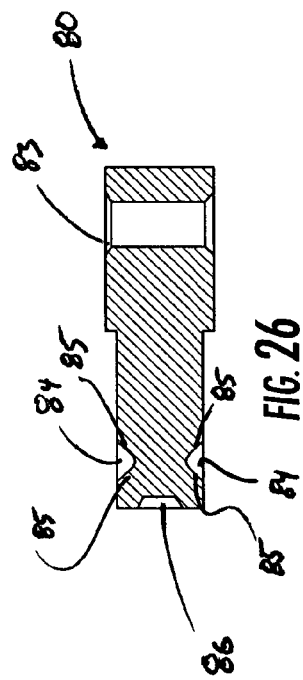

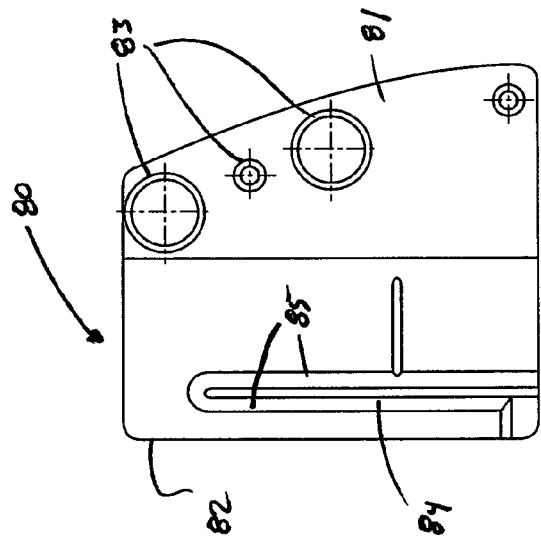
FIG. 29
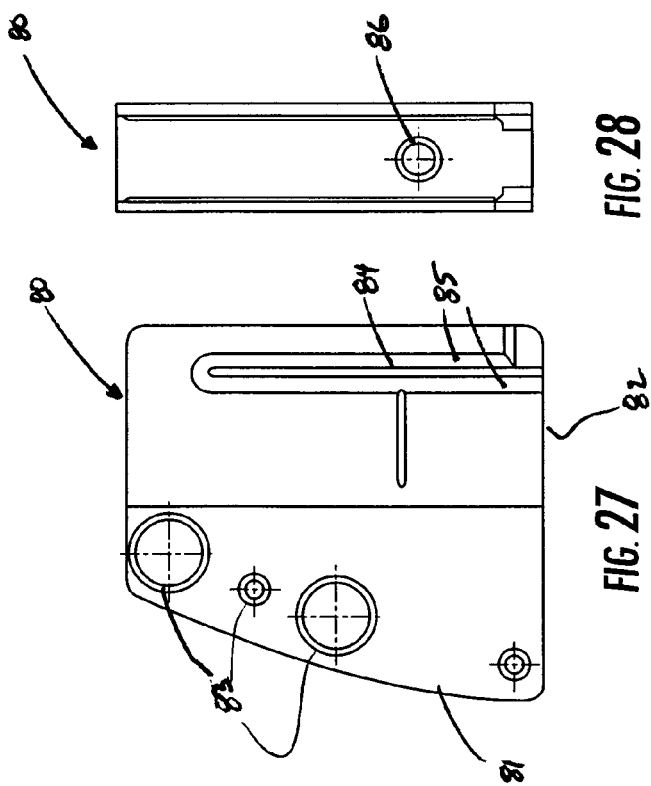
FIG. 28
FIG. 27
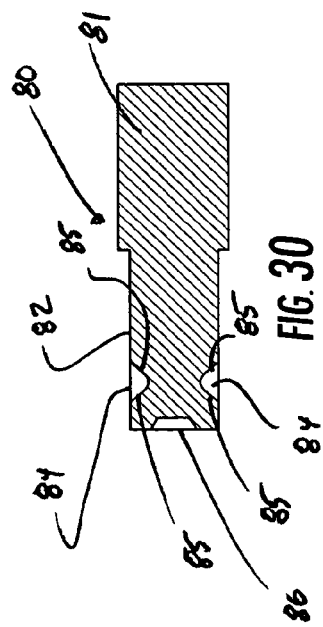
FIG. 30

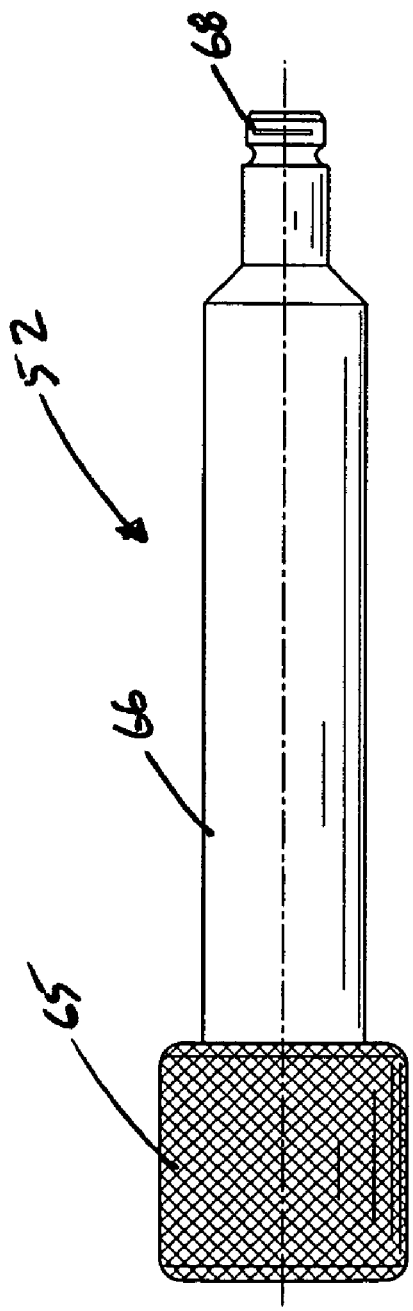
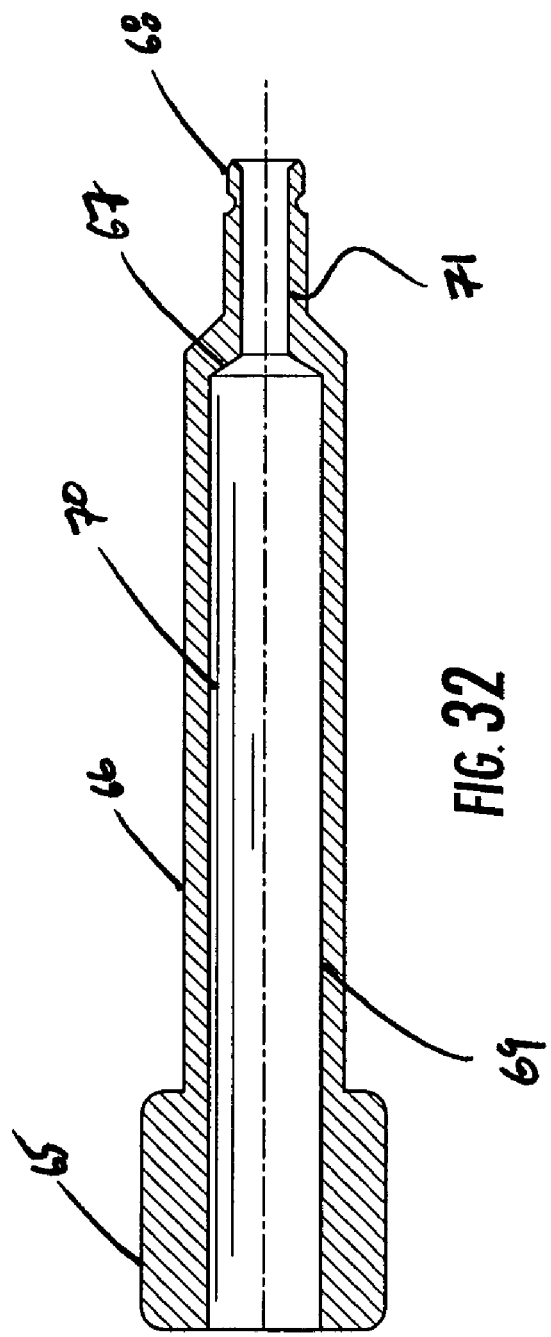
FIG. 31
FIG. 32

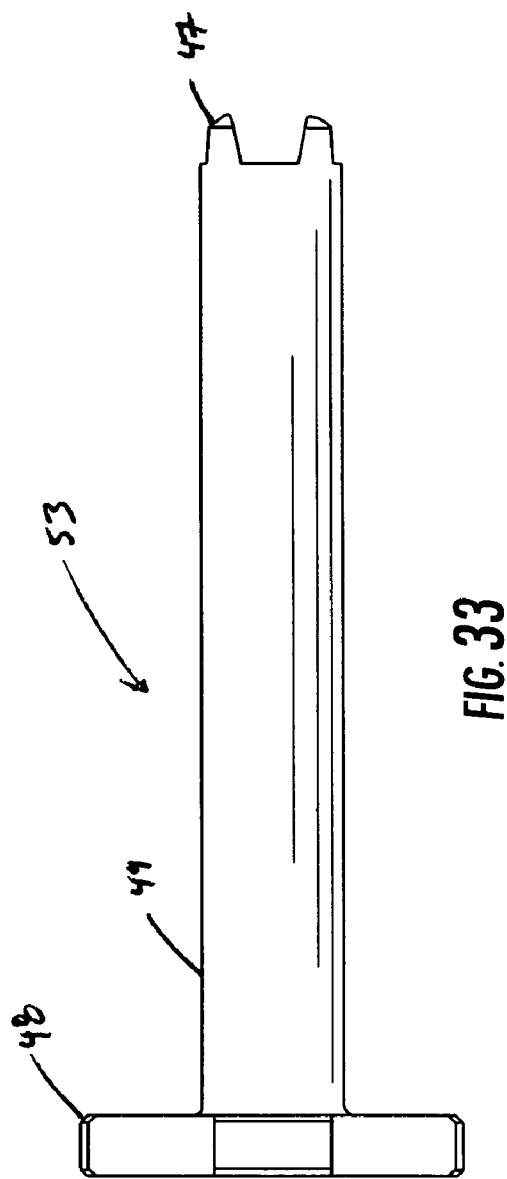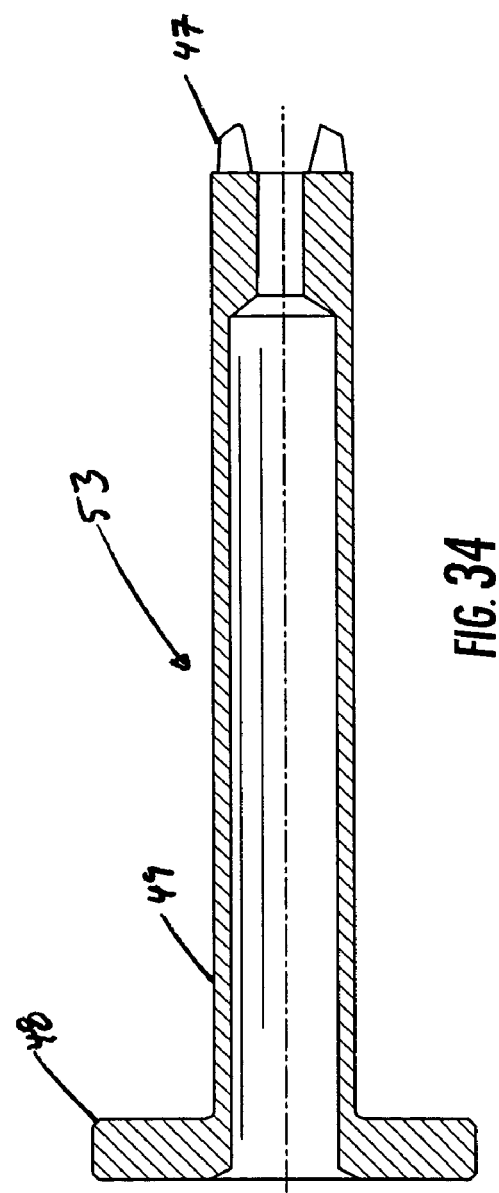

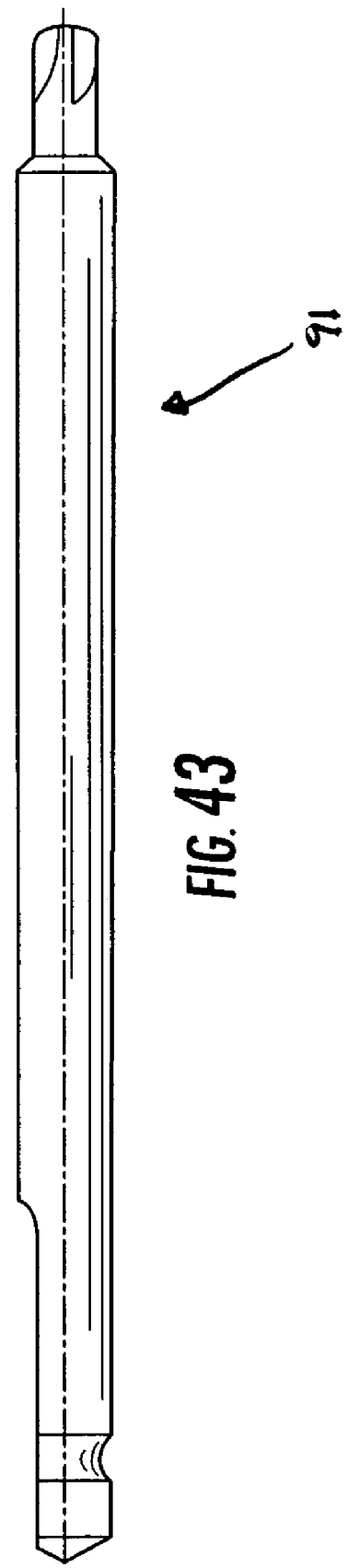
FIG. 42
FIG. 43

GUIDE ASSEMBLY FOR INTRAMEDULLARY FIXATION AND METHOD OF USING THE SAME

BACKGROUND OF THE INVENTION

1. Field of the Invention

The present invention is related to the use of orthopedic fixation devices and devices for installing the same, and in particular, to intramedullary fixation devices and guides for facilitating installation and fixation of the same.

2. Description of Related Art

Long bone fractures are fairly common in the elderly population, often due to the onset of osteoporosis. Long bone fractures may be reduced by the use of assorted conventional bone plates. For example, a bone plate may be attached to the outside surface of two adjacent fragments of a long bone and then secured by inserting bone screws through openings in the bone plate. Problems may arise with such bone plates, however, in that the soft tissues covering the bone plates may become irritated by passage or movement over the bone plates.

An alternative to bone plates are intramedullary nails or rods that extend through a medullary canal defined within the fractured long bone. The nails or rods are typically fastened to the fractured portions of the long bones with bone screws. The nails or rods are placed into the medullary canal by insertion through a hole which is drilled into one end of the long bone. For instance, to reduce a fractured femur with an intramedullary rod or nail, a hole is drilled through the articular cartilage between the condyles to provide access for the rod. Because the intramedullary nails or rods are contained within the medullary canal, they avoid the problems with soft tissue associated with plates. However, insertion of these rods through holes in the ends of the longs bones requires damaging the articular cartilage on the ends of the long bones.

U.S. Pat. No. 6,527,775 to Warburton ("the '775 patent"), which is hereby incorporated herein in its entirety by reference, describes an intramedullary fixation device used to reduce a distal fracture of the radius. As shown in FIG. 3A of the '775 patent, the intramedullary fixation device 25 includes an elongated axially extending rod 26 with a distal portion 27 and a proximal portion 28. The fixation device also includes a distal fixation member 30 and proximal fixation members 35. The distal fixation member extends through the distal portion of the rod and into a distal fracture fragment 18. The proximal fixation members extend through the proximal portion of the rod and the portion of the radius proximal the fracture line. The '775 patent describes avoiding end insertion of the rod through the cartilage of the distal radius by using a laterally positioned bone window 16 defined in the distal fracture fragment.

Although the '775 patent discloses an intramedullary fixation device for reducing a distal radius fracture without insertion through cartilage on the end of the distal radius, other long bones, such as the humerus, femur and tibia are also often fractured and require repair.

Therefore, it would be advantageous to have a fixation device for all long bones that is insertable into the medullary shaft of the long bones. It would also be advantageous if the fixation device were capable of insertion without damaging the articular cartilage of the long bones.

BRIEF SUMMARY OF THE INVENTION

The present invention addresses the above needs and achieves other advantages by providing an intramedullary fixation assembly usable with different long bone types and a guide assembly for guiding deployment of the intramedullary fixation assembly. The intramedullary fixation assembly includes a fixation member that has ends and a curved body extending between the ends. The curved body of the fixation member has a radius of curvature extending from a first end configured to extend between a side aperture defined in a first fragment through the medullary canal and into a second fragment, regardless of the type of the long bone. Fasteners are used to fix the fixation member to the bone fragments and are guided by a guide assembly. The guide assembly includes a guide body defining openings configured to guide the fasteners through openings defined in the fixation member and into the bone fragments. A fixation end of the guide body includes a pair of opposing, converging surfaces that are configured to engage in a positive fit with an exposed end of the fixation member accessible through the side aperture in the first fragment. Advantageously, the positive fit facilitates accurate positioning of the guide body and, as a result, of the fixation member fasteners.

In one embodiment, the present invention includes an intramedullary fixation assembly for repairing any of a plurality of long bone types. Each of the long bones defines a medullary canal fractured into at least a first and second adjacent bone fragments. The first bone fragment has a free end with an articular cartilage surface and defines a side aperture. The side aperture is positioned subjacent the articular cartilage surface of the first bone fragment and extends into the medullary canal. Included in the intramedullary fixation device are a plurality of fasteners (e.g., a first fastener and a second fastener) each having an elongate body with a head end and an opposite, bone-securing end. A fixation member of the intramedullary fixation device includes a first end, a second end and a curved body extending between the first and second ends. The curved body defines at least one fastener opening positioned proximate the first end and configured to allow passage of the first fastener therethrough and into the first bone fragment. Also defined by the curved body is a second fastener opening positioned proximate the second end and configured to allow passage of the second fastener therethrough and into the second bone fragment. The curved body has a radius of curvature extending from the first end that is configured to allow passage of the fixation member through the side aperture of the first bone fragment and into the medullary canal until the first end of the fixation member is positioned adjacent the side aperture, and within a portion of the medullary canal defined within the first bone fragment, and the second end of the fixation member is positioned within a portion of the medullary canal defined within the second bone fragment. In this manner, the fixation assembly can be used to reduce and secure a fracture of any of the various types of human long bone types.

In one aspect, the curved body has a smooth, continuous curvature that extends from its first end to its second end. The radius of curvature is preferably defined by a centerline extending from the first end to the second end. Also, the curved body preferably includes smoothly curving concave and convex sides configured to facilitate passage of the fixation member through the side aperture and into the medullary canal. Also, the first and second ends may be tapered to facilitate insertion through the side aperture and into the medullary canal.

In another aspect, the same radius of curvature extending from the first end can be used for a plurality of lengths for the curved body, allowing the design to be extended to various long bone types. Preferably, the radius of curvature extending from the first end ranges from between 1.5 to 5 inches, and more preferably, about a radius of curvature of approximately 2 to 4 inches, or 2.6 to 3.4 inches.

In another embodiment, the present invention includes a guide assembly for facilitating placement of a plurality of bone fasteners of an intramedullary fixation assembly through predefined locations on a fixation member of the intramedullary fixation assembly. The fixation member extends through a medullary canal defined within a long bone and has an exposed end accessible through a side aperture defined by the long bone. Included in the guide assembly is at least one guide fastener configured to extend into the exposed end of the fixation member so as to be secured to the fixation member. A guide body includes a fixation end and defines a plurality of fastener guide openings. These guide openings are configured to orient the bone fasteners extending through the guide openings with the predefined locations on the fixation member. The fixation end defines an opening configured to allow passage of the guide fastener through the guide body and into the exposed end of the fixation member. The fixation end includes at least one pair of surfaces positioned opposite each other and generally extending in a converging direction. These surfaces are, as a result, configured to engage in a positive fit with the exposed end of the fixation member when the guide body is secured thereto with the guide fastener. This positive fit reduces the motion between the guide body and the fixation member, thereby improving the ability of the guide openings to accurately guide the bone fasteners through the predetermined locations on the fixation member.

As an example of the surfaces used for a positive fit, the pair of surfaces may be portions of a convex surface or prong configured to extend within a concave surface defined within the exposed end of the fixation member. Preferably, the convex surface is configured to reach a positive fit prior to full contact between the remaining (non-convex and non-concave) surfaces of the fixation end and the exposed end. In yet another aspect, there may be additional pairs of surfaces or prongs configured for a positive fit, including second, third and fourth pairs of surfaces spaced from each other in a cruciform configuration.

The present invention has many advantages. For example, the invention has many attributes that facilitate its use for different types of human long bone. Maintaining a constant radius of curvature of a first end of the curved body allows for different sized long bones and different types of long bone to be accommodated merely by extending the arc further to produce a greater "hook" on increasing sizes of fixation members. This overcomes the increase in not only the length of the long bone, but also the increase in distance between widened end and width of the medullary canal, facilitating its use on different and larger types of long bones. It has also been determined that use of a radius of curvature in the ranges of 1.5 to 5 inches facilitates use with different types of long bone, especially when the curved body curves continuously along its length and the ends are tapered for easy insertion. The use of a cruciform shape and positive fit or wedge effect used for the concave indentations and the prongs provides rotational and translational stability of the fixation member when attached to the guide assembly. In addition, the positive fit or wedge effect operates to center and reduce micro-motion between the targeting guide and the rest of the guide assembly.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 3 is a side elevation view of a fixation member of the intramedullary fixation assembly of FIG. 1;

FIG. 4 is another side elevation view of a fixation member of the intramedullary fixation assembly of FIG. 1;

FIG. 5 is another side elevation view of a fixation member of the intramedullary fixation assembly of FIG. 1;

FIG. 6 is another side elevation view of a fixation member of the intramedullary fixation assembly of FIG. 1;

Figure 1:
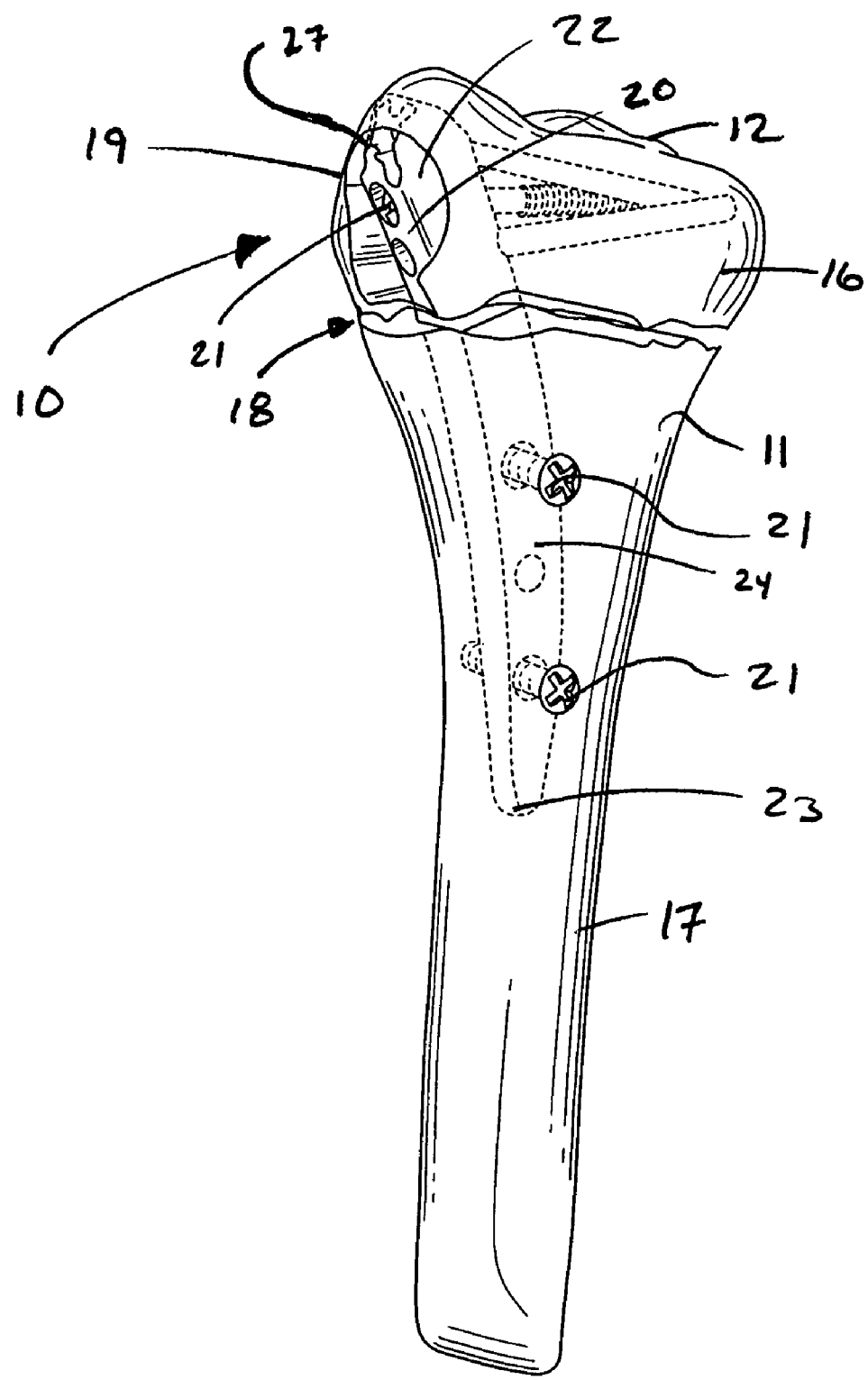
FIG. 1 is a perspective view of a long bone fracture repaired using an intramedullary fixation assembly of one embodiment of the present invention.
Figure 11:
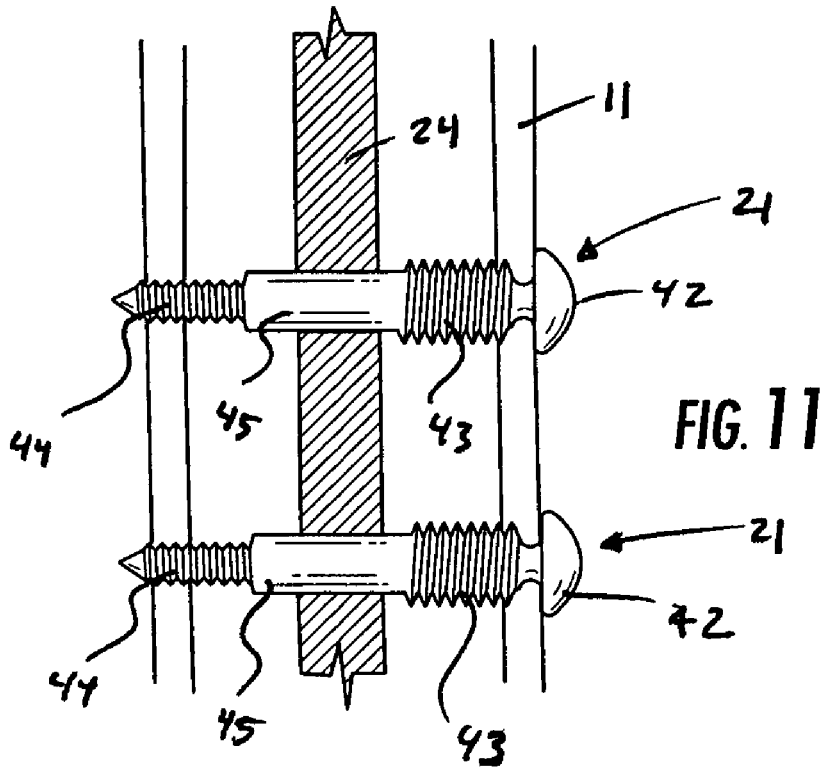
Figure 12:
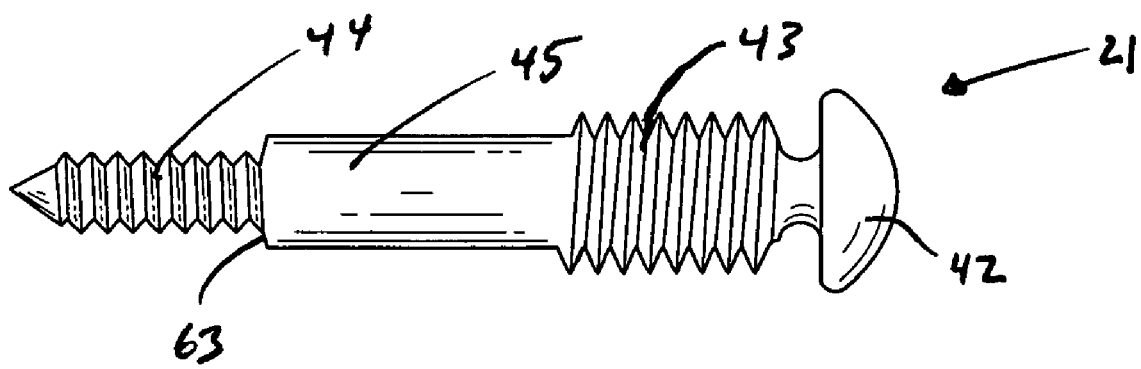
Figure 14:
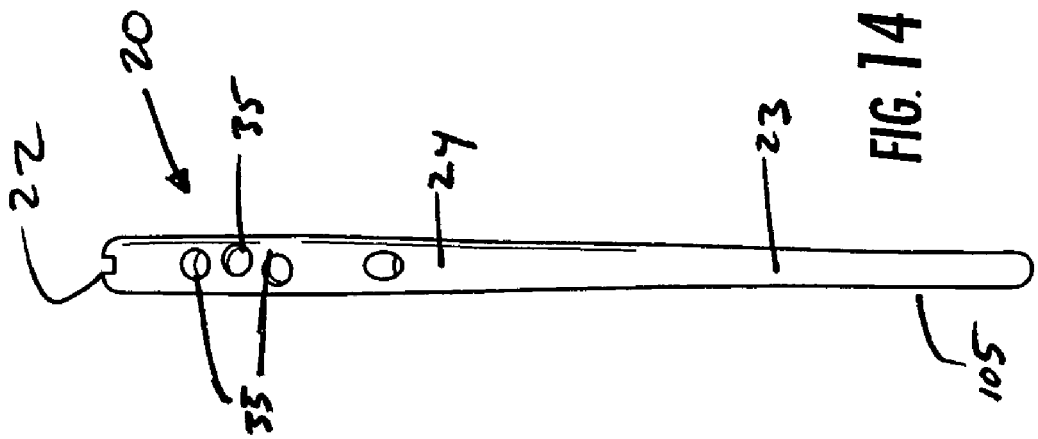
Figure 13:
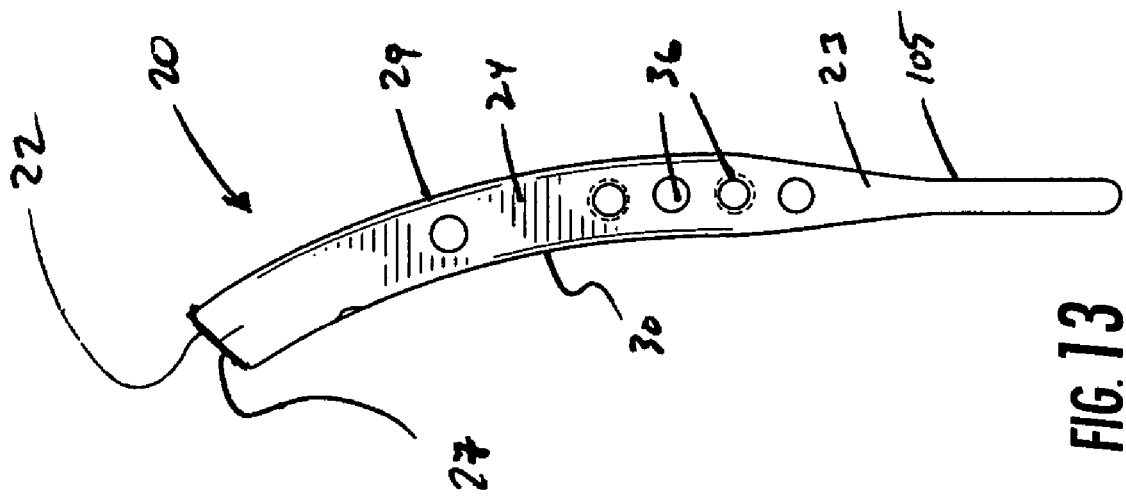
Figure 19:
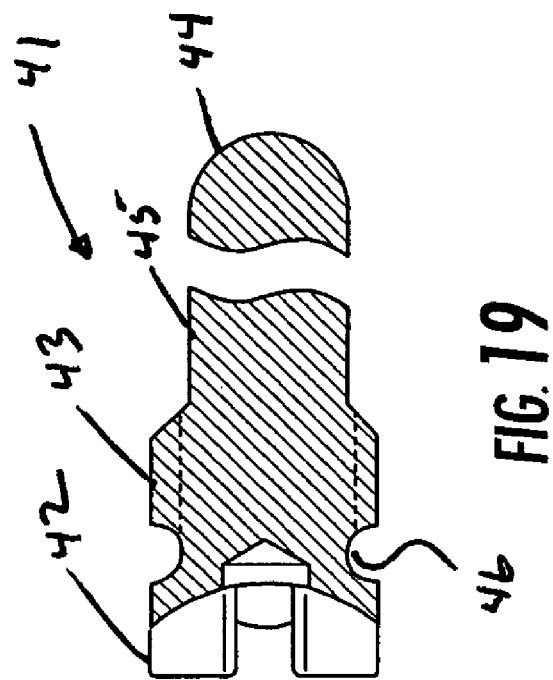
Figure 18:
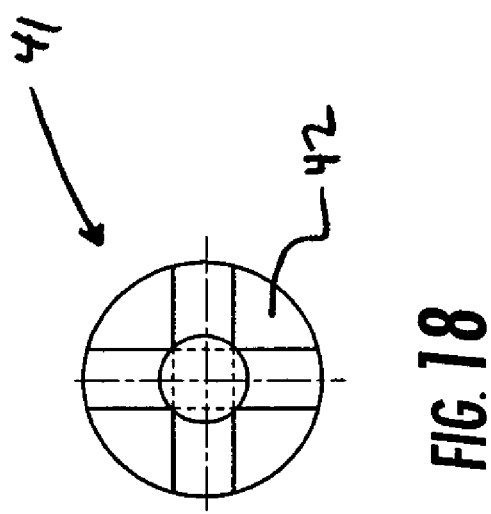
Figure 35:
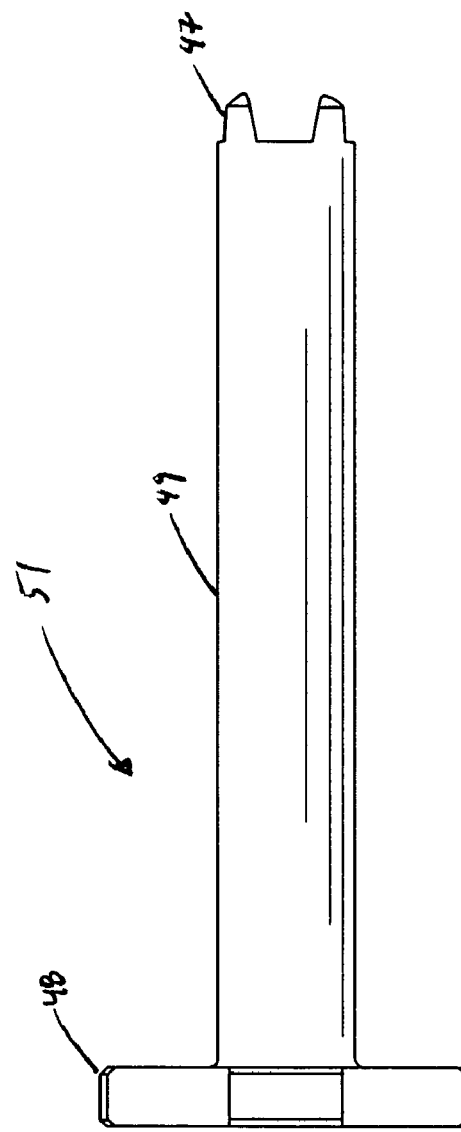
Figure 36:
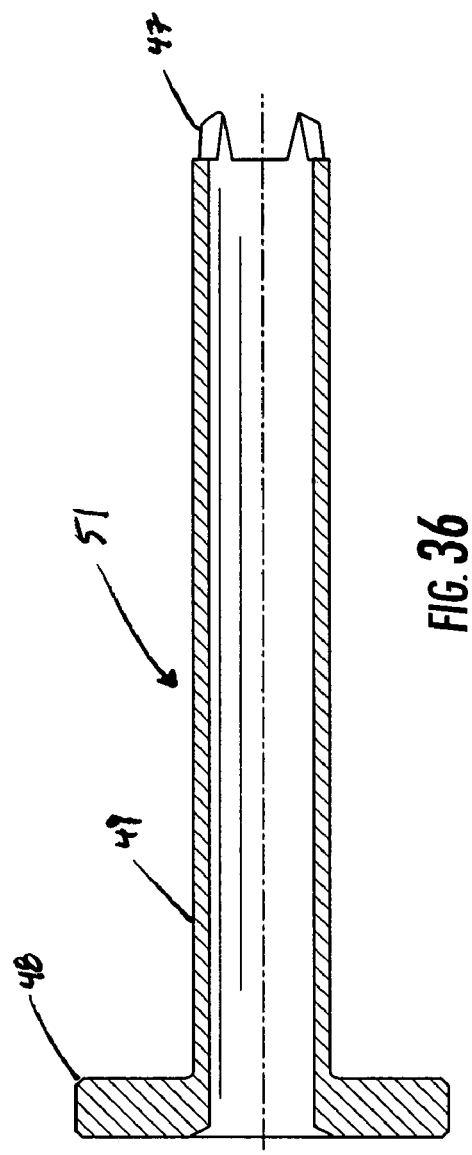
Figure 37:
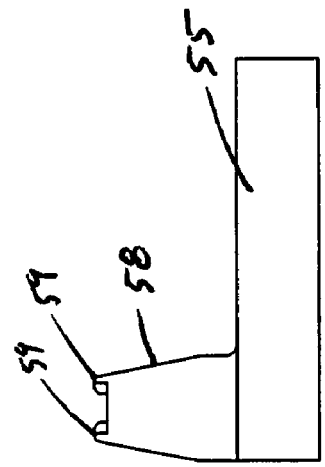
Figure 41:
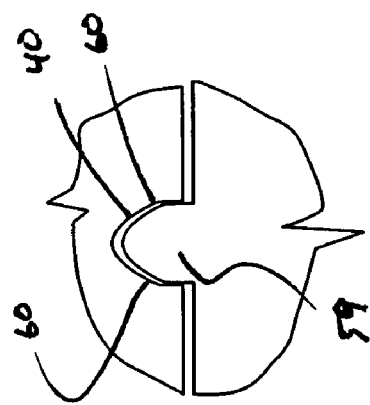
Figure 38:
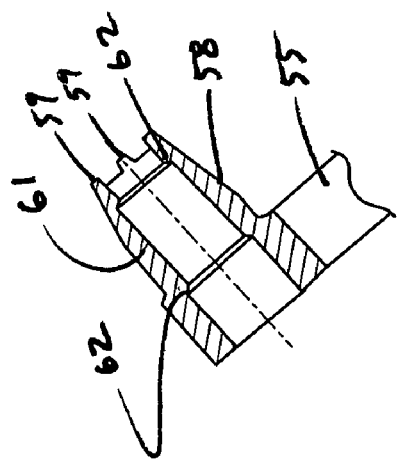
Figure 39:
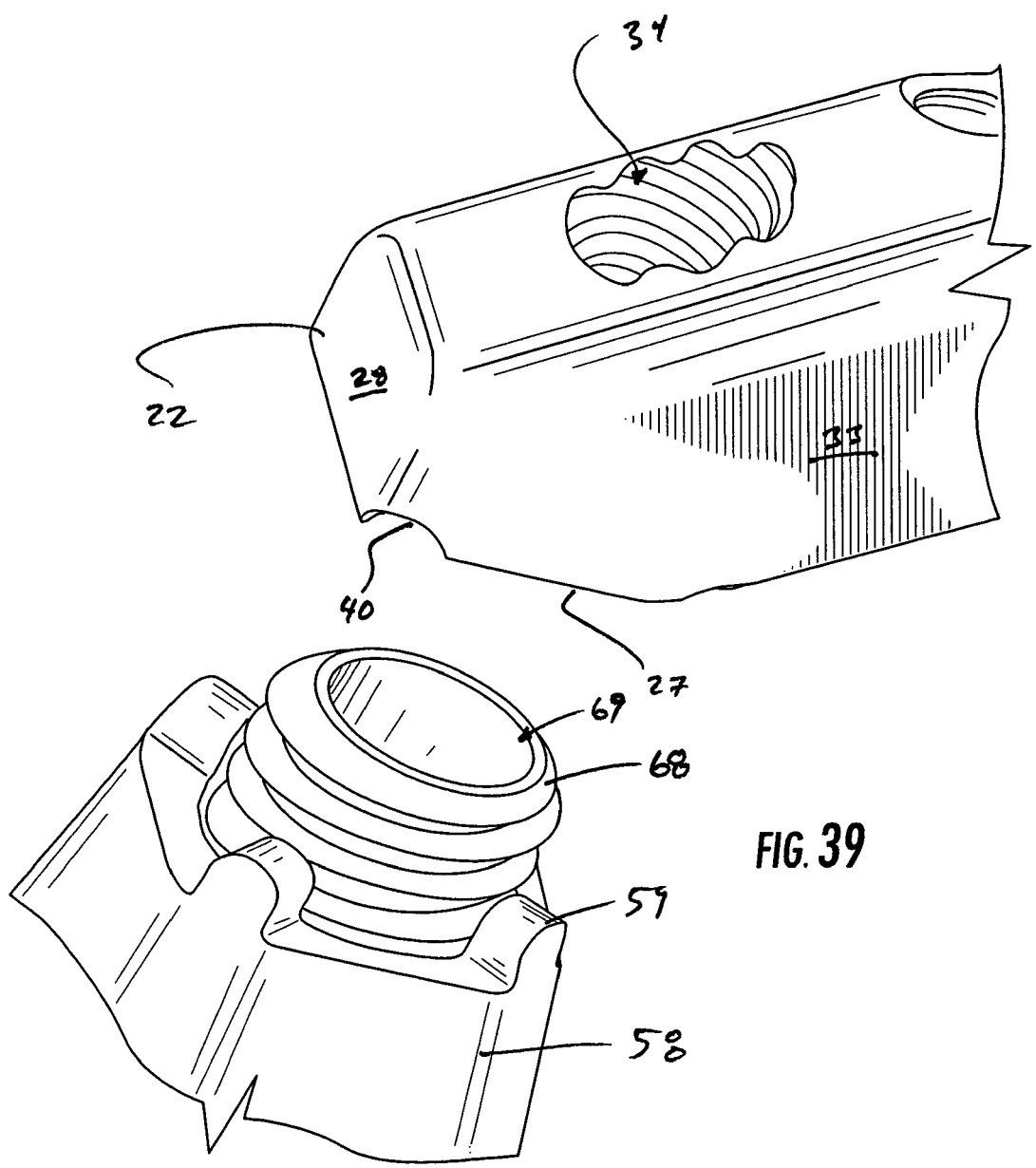
Figure 40:
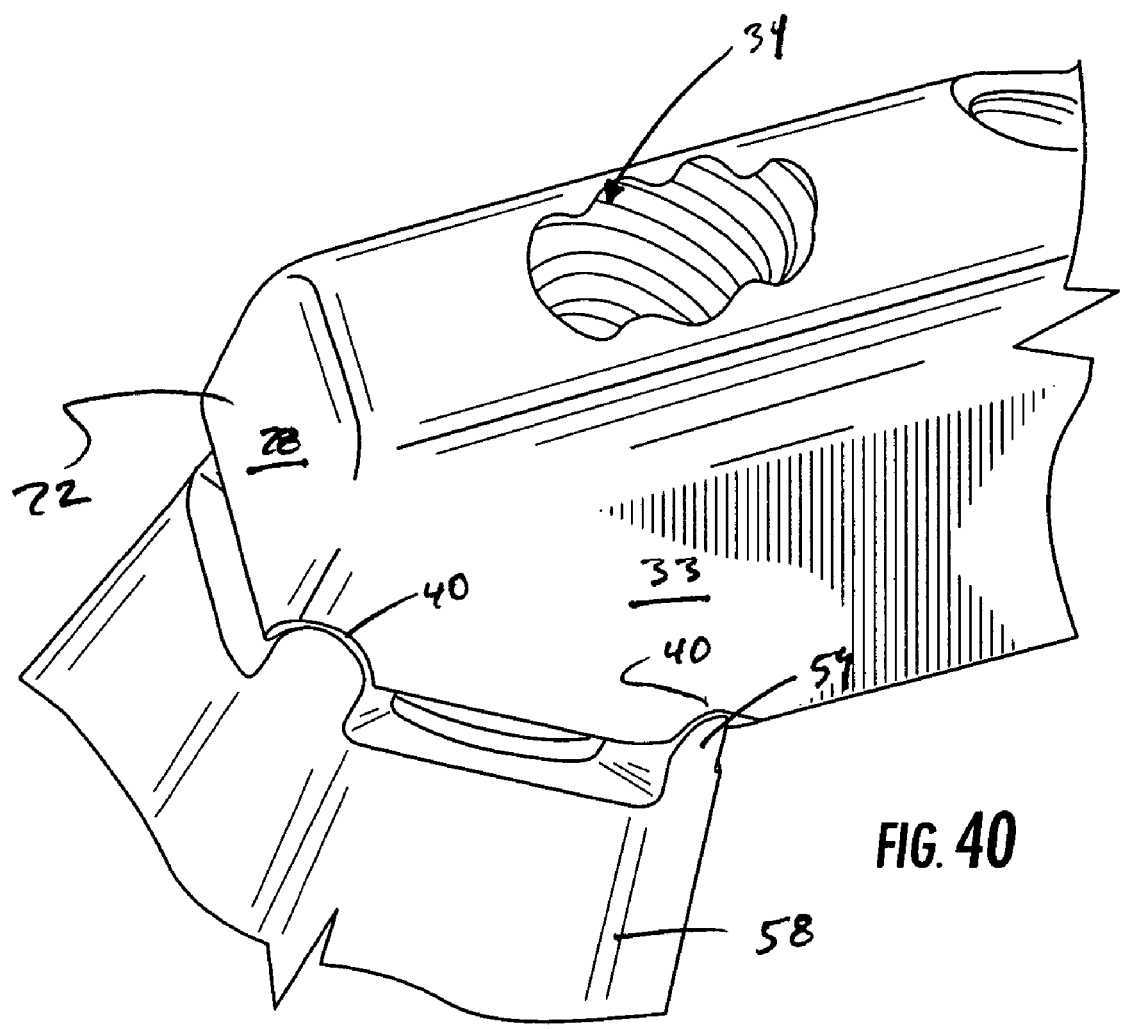
Figure 44:
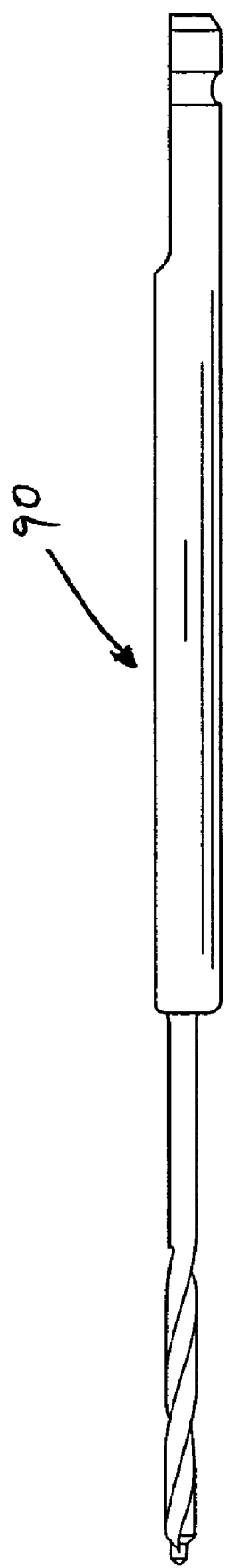
Figure 46:
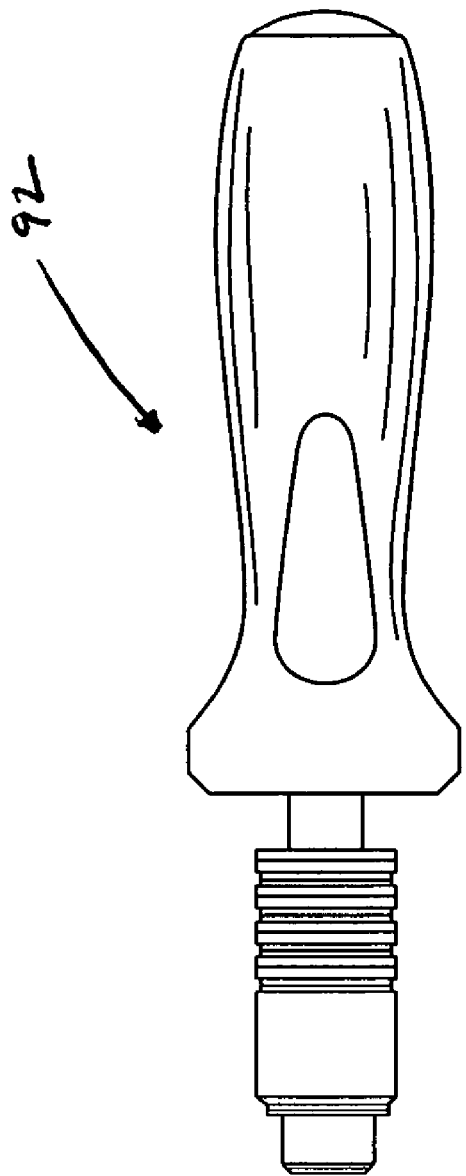
Figure 45:
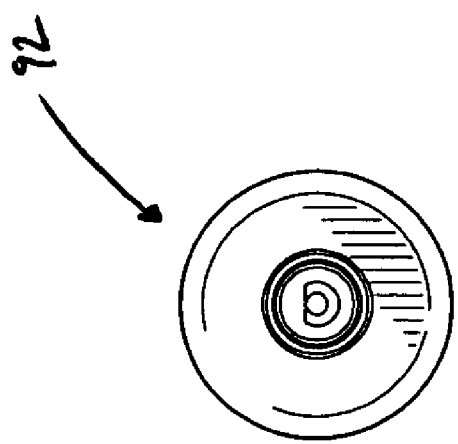
Figure 47:
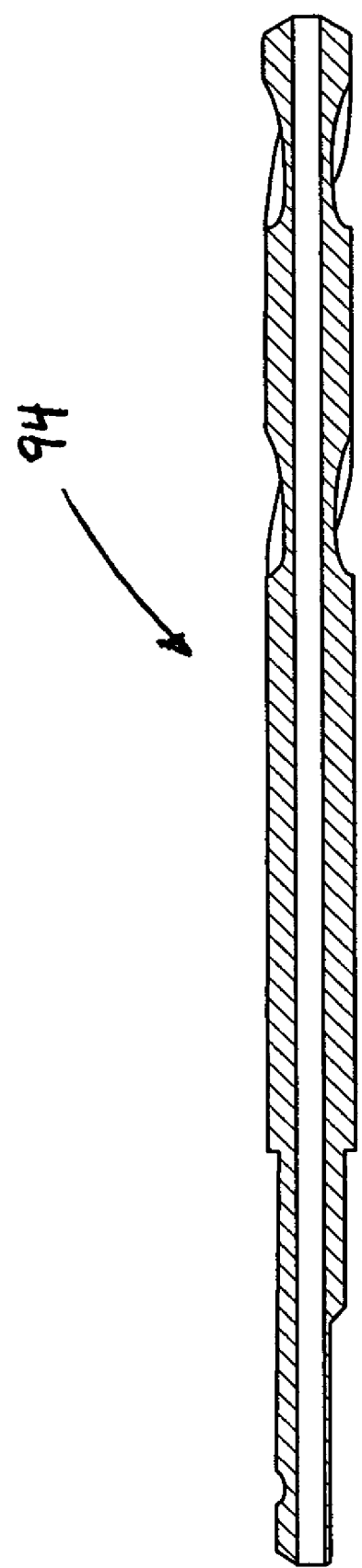
Figure 48:
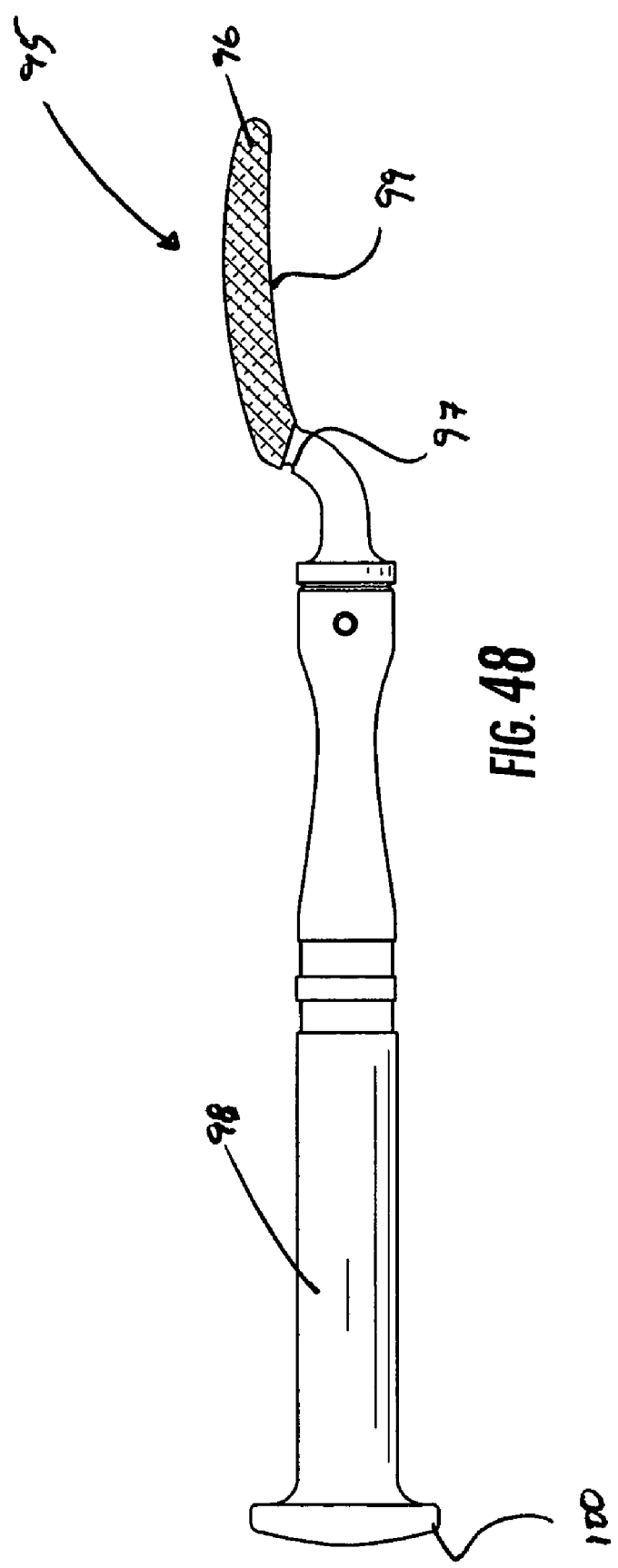
Figure 49:
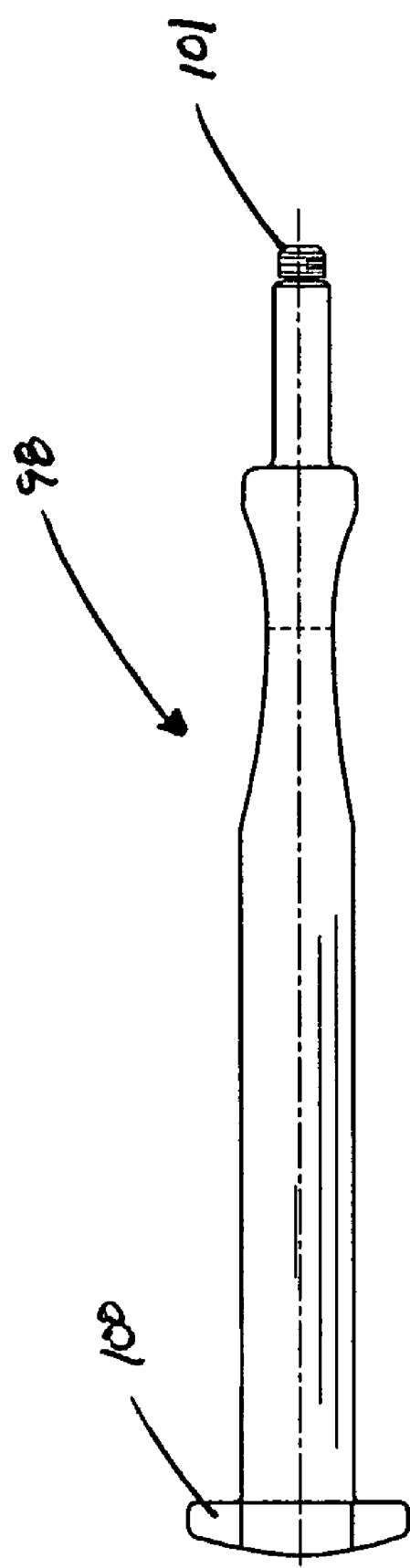
Figure 50:
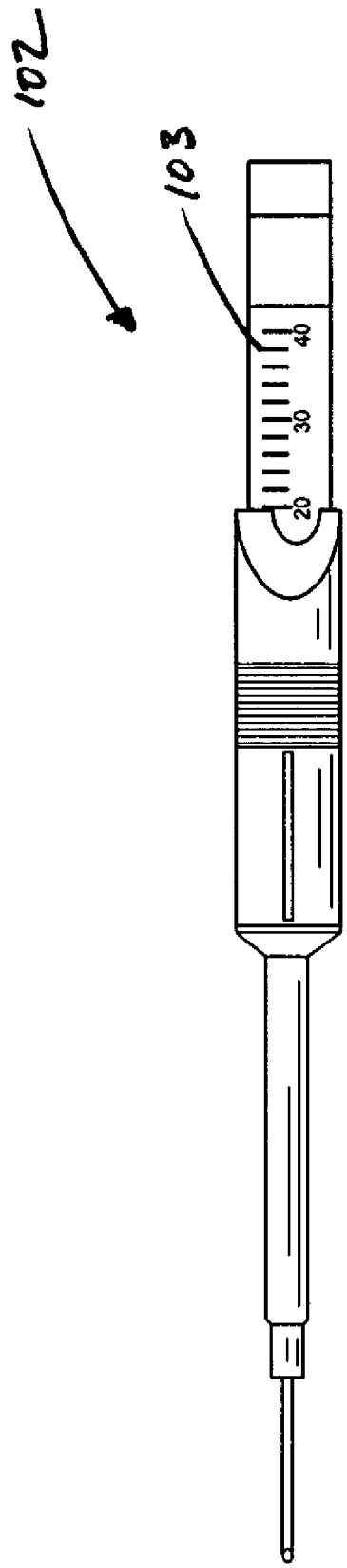
Figure 51:
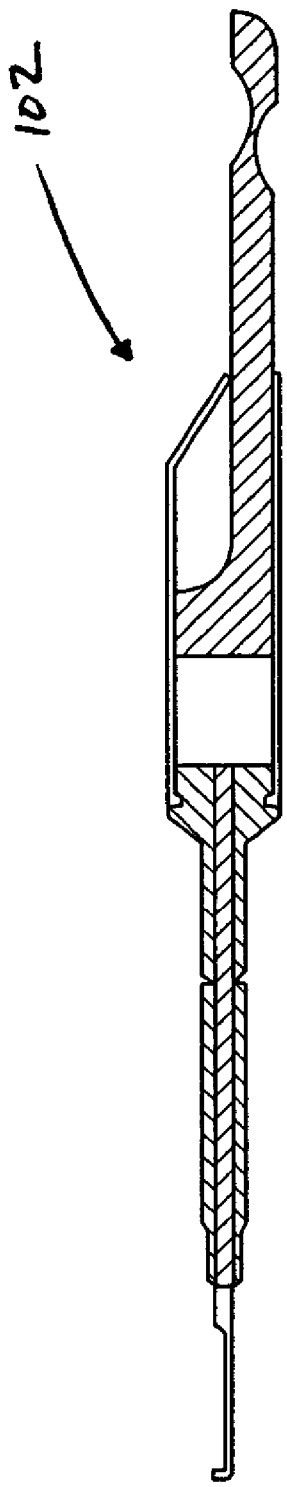
Figure 52:
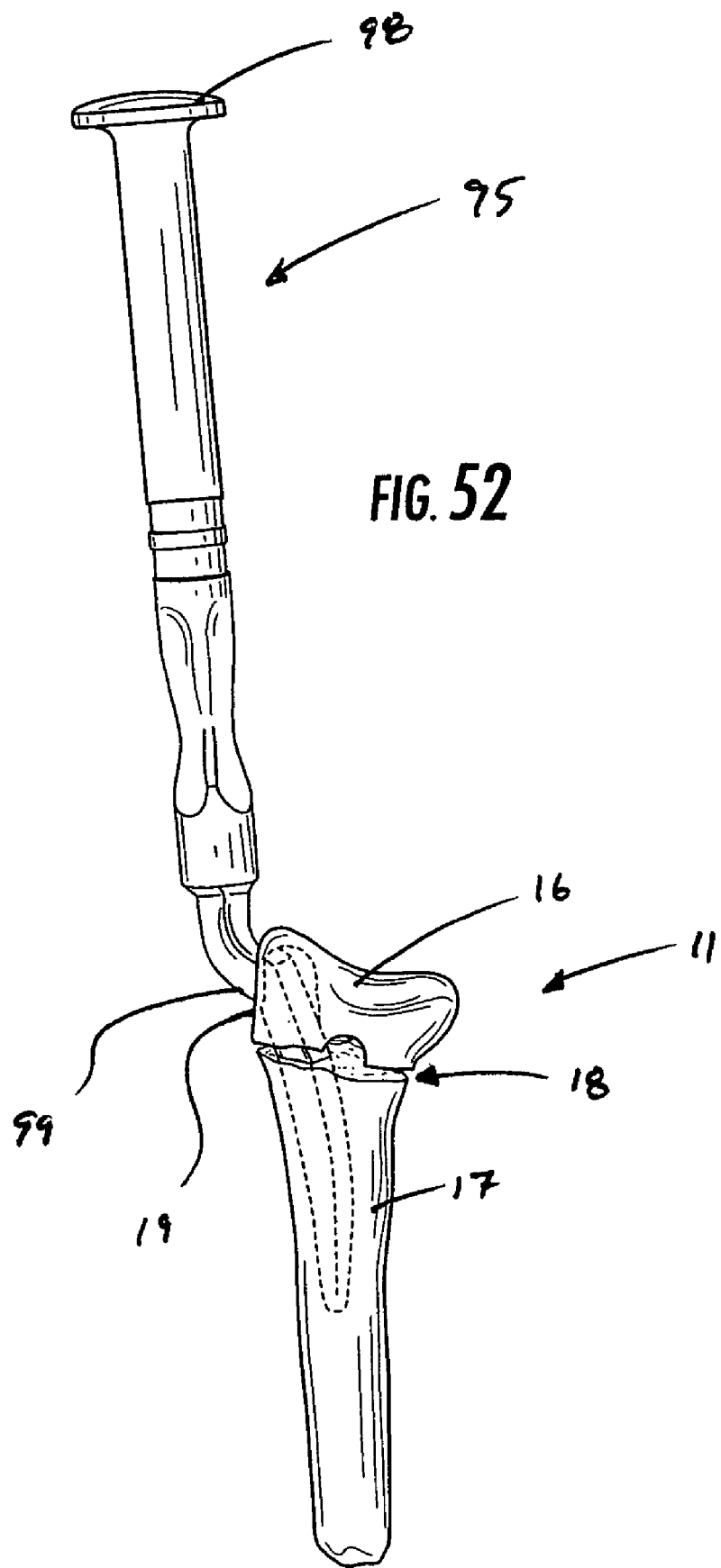
Figure 53:
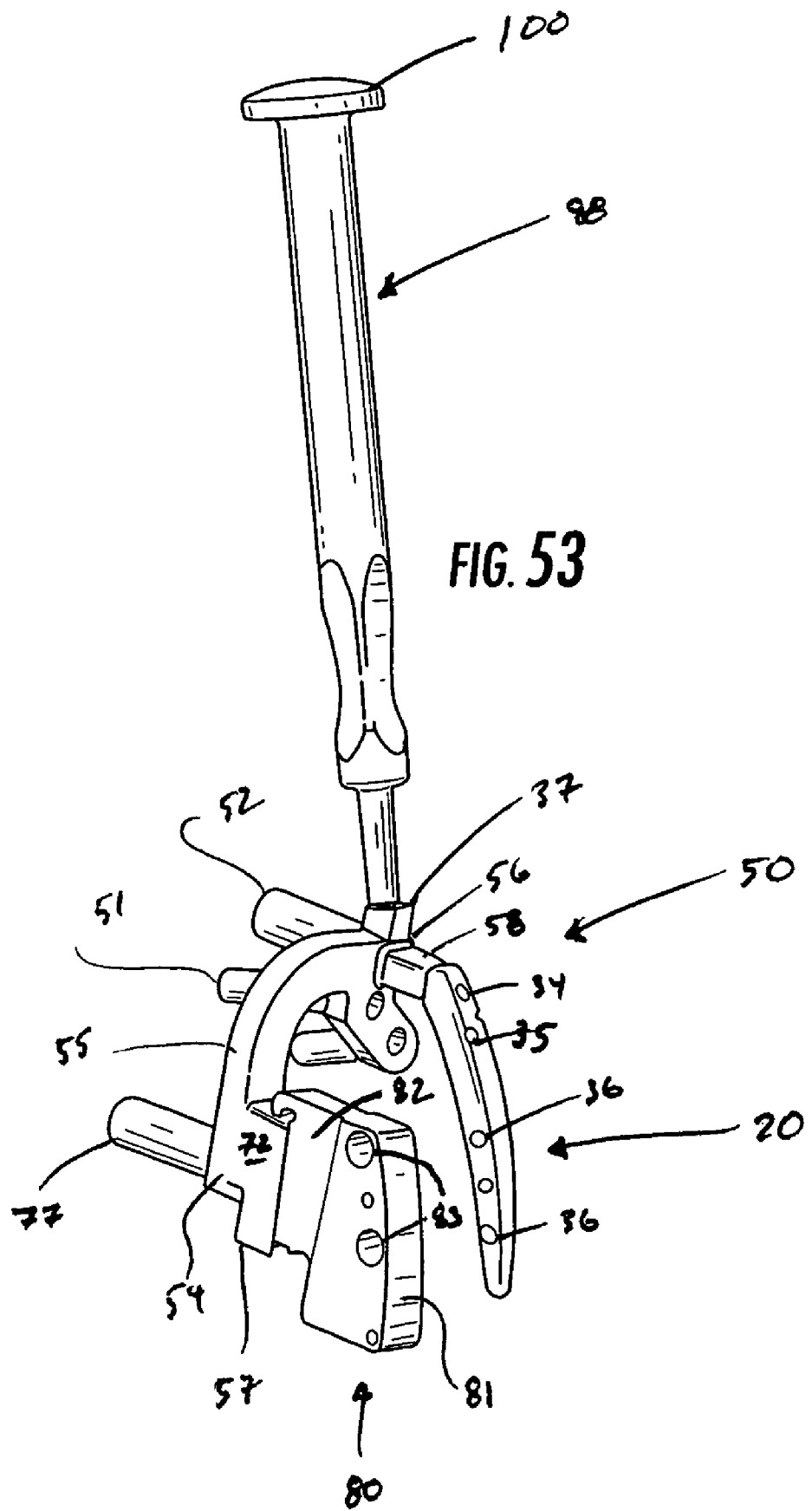
Figure 54:
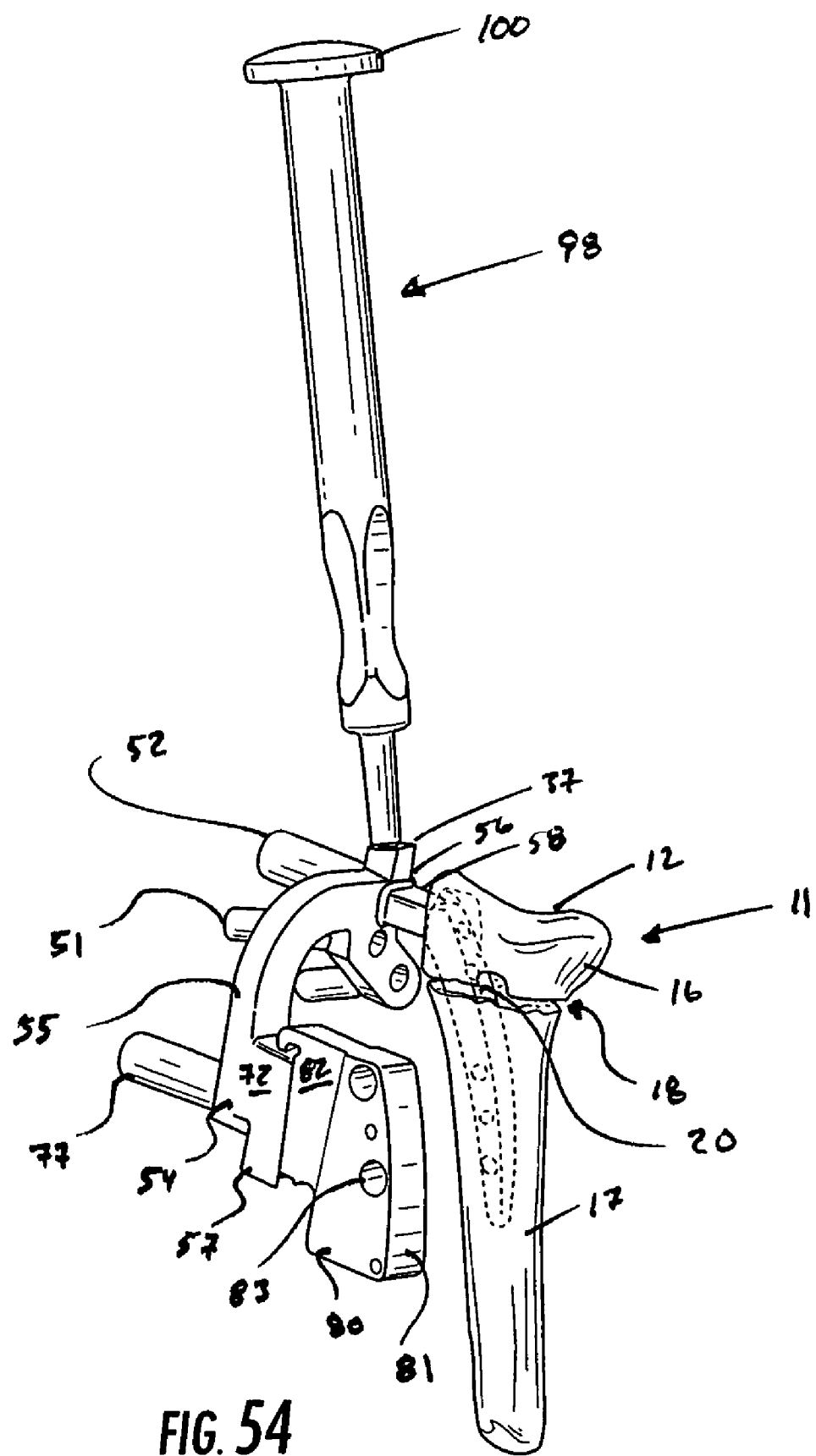
Figure 55:
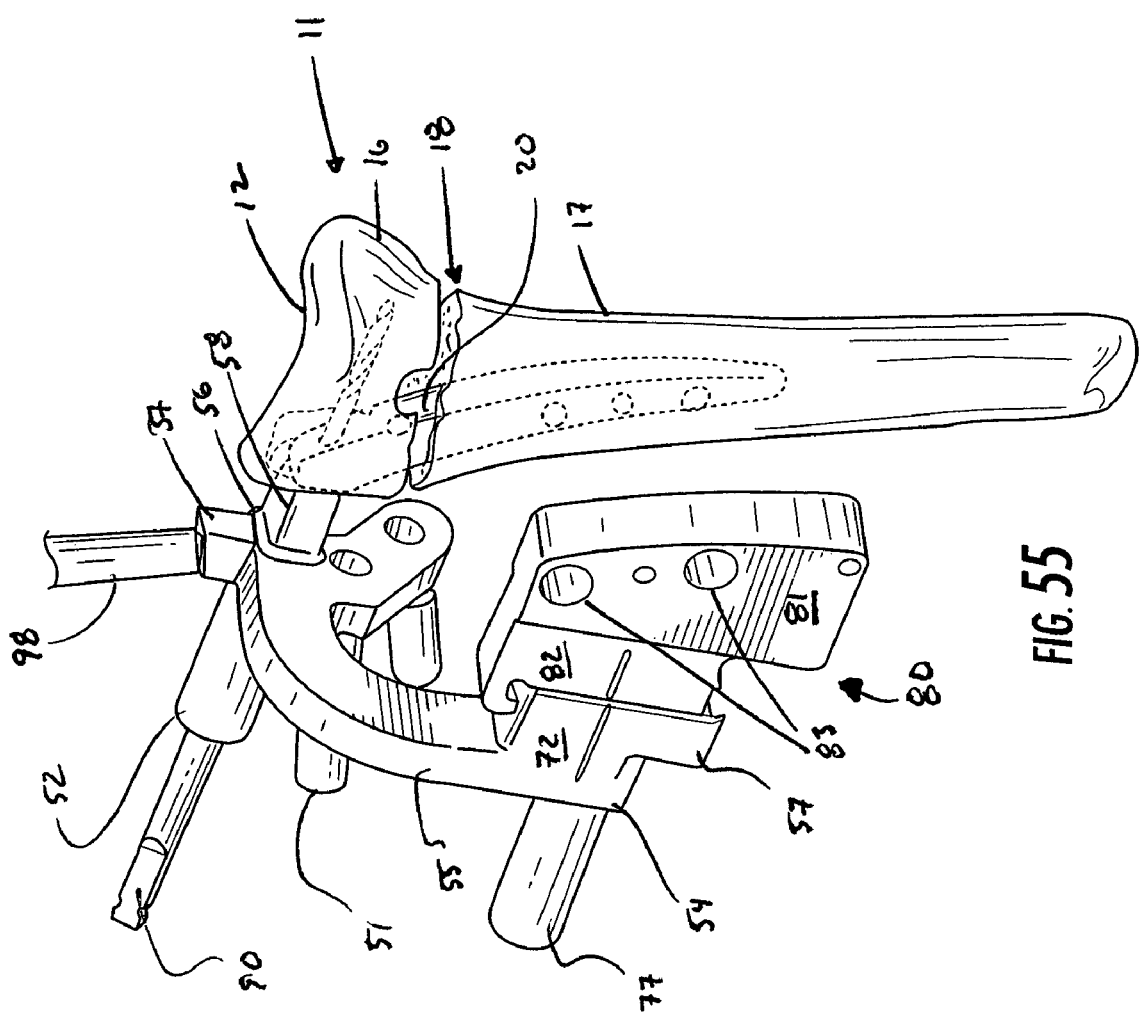
Figure 56:
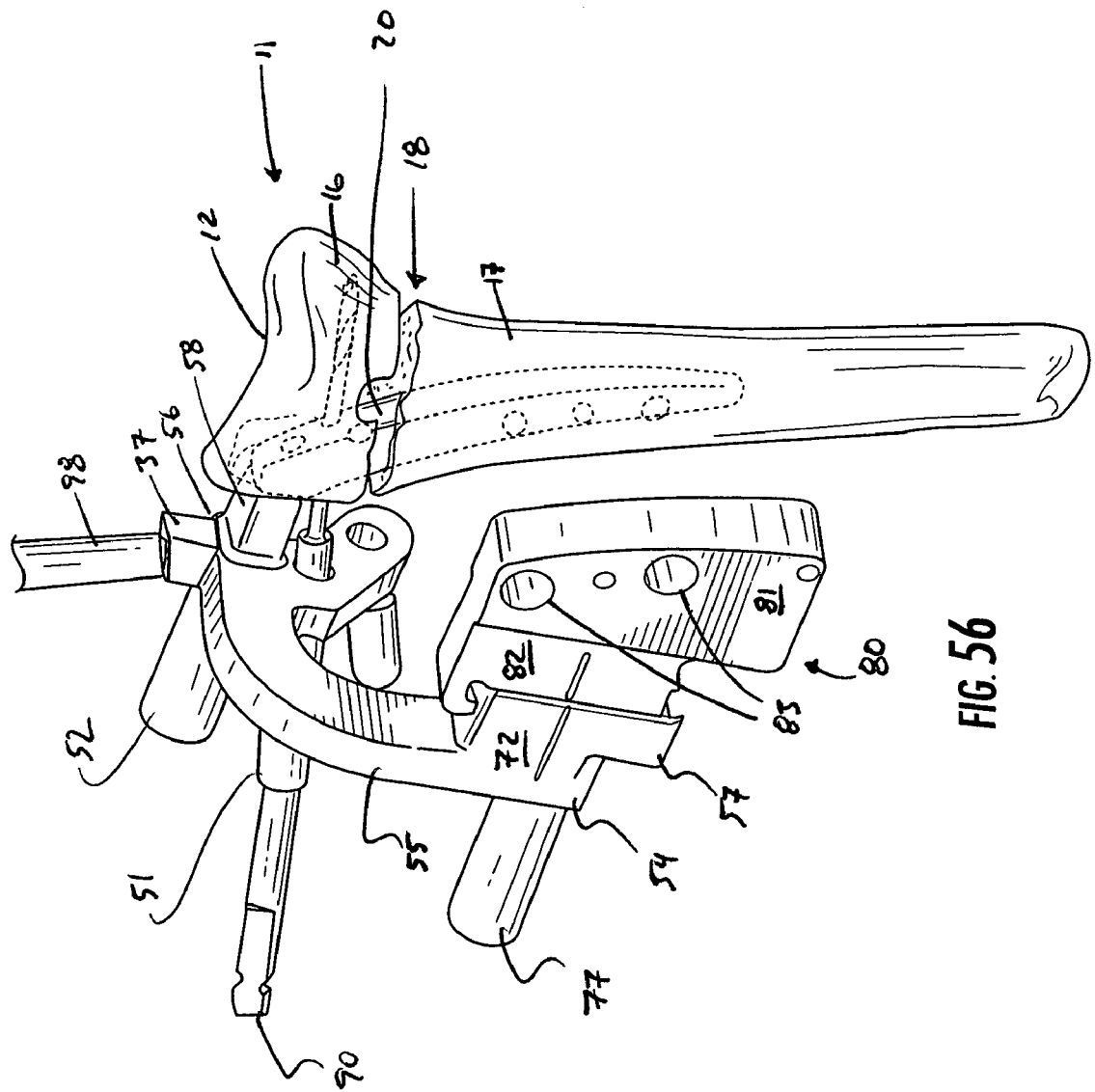
Figure 57:
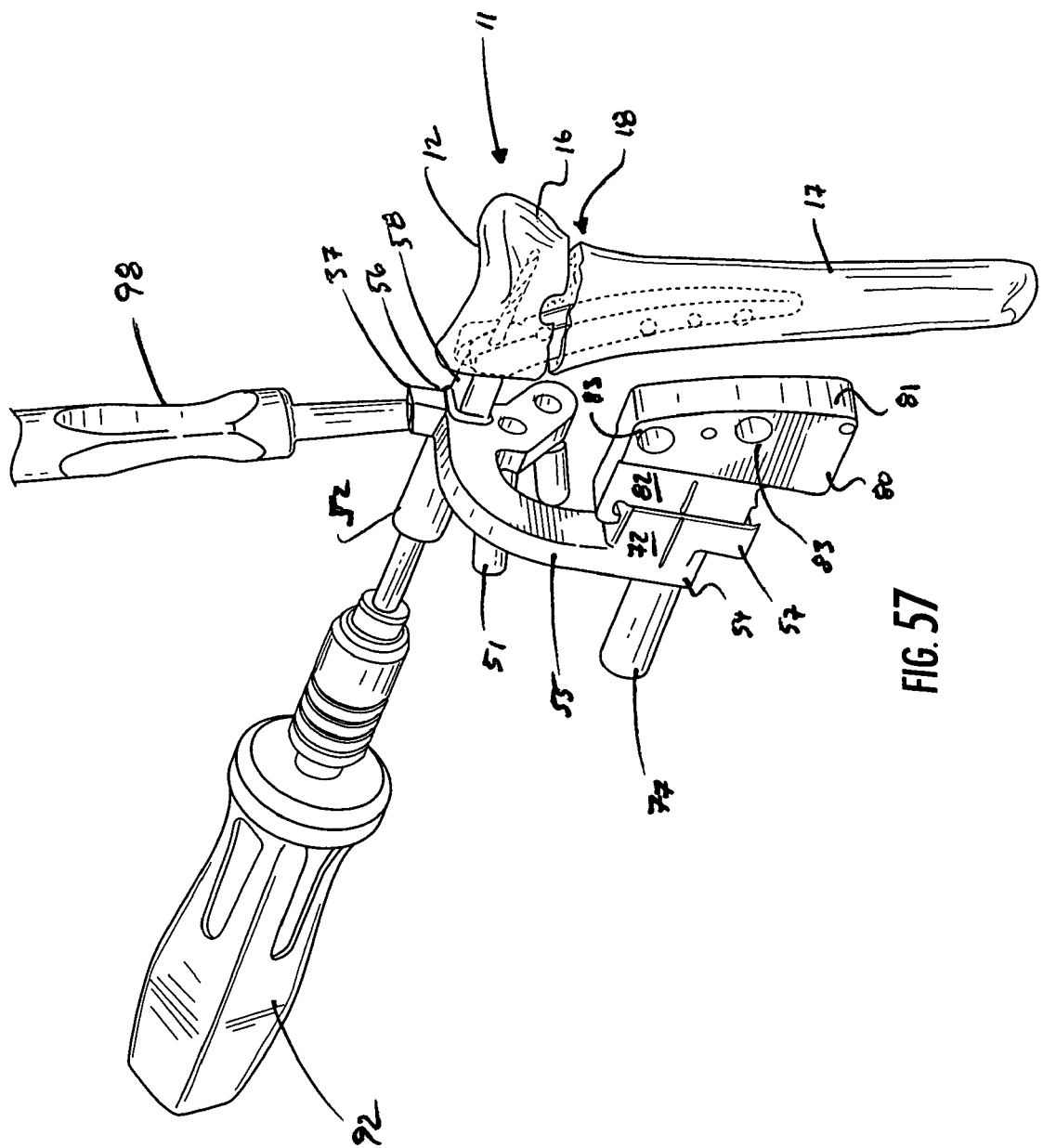
Figure 58:
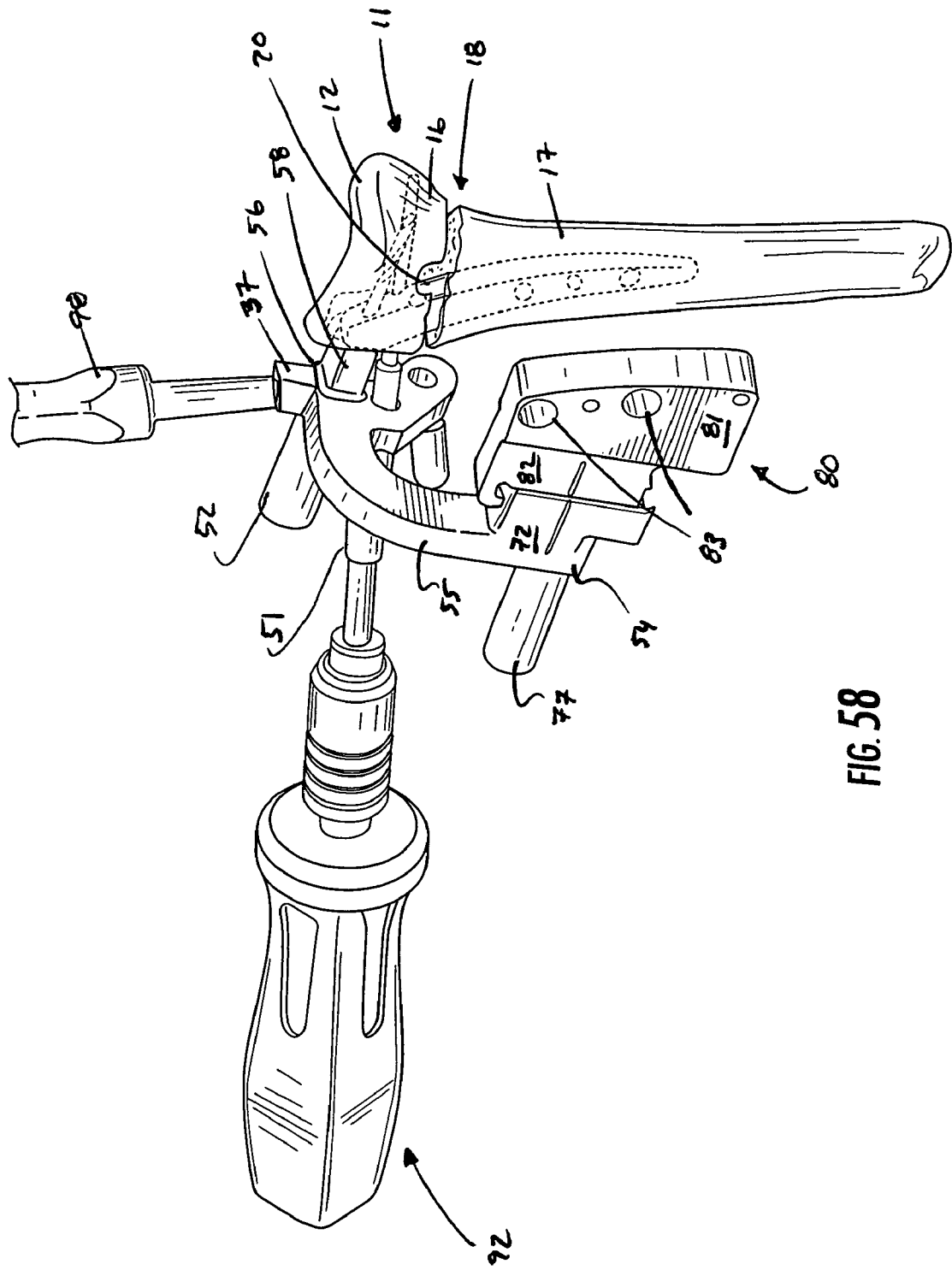
Figure 59:
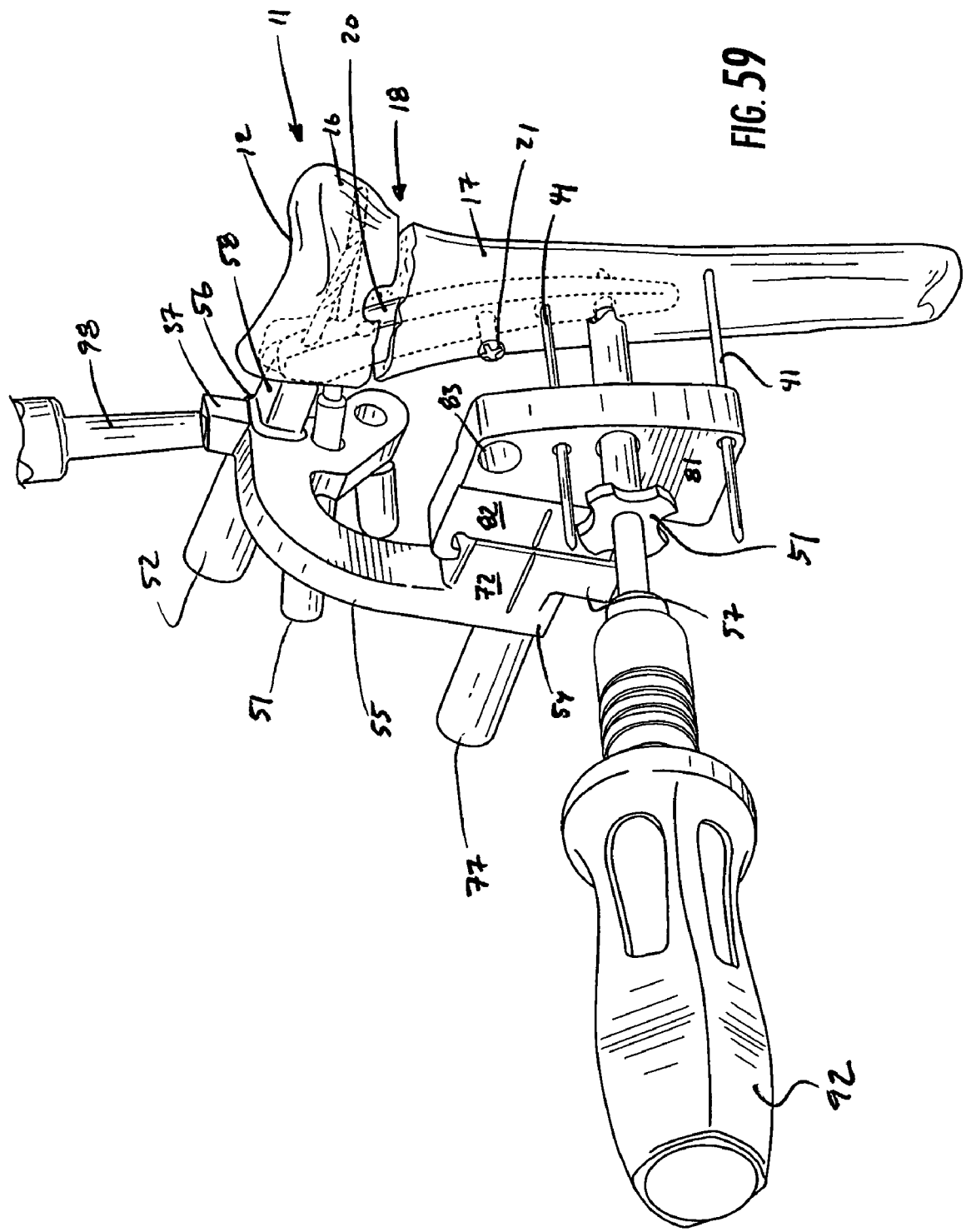
Figure 60:
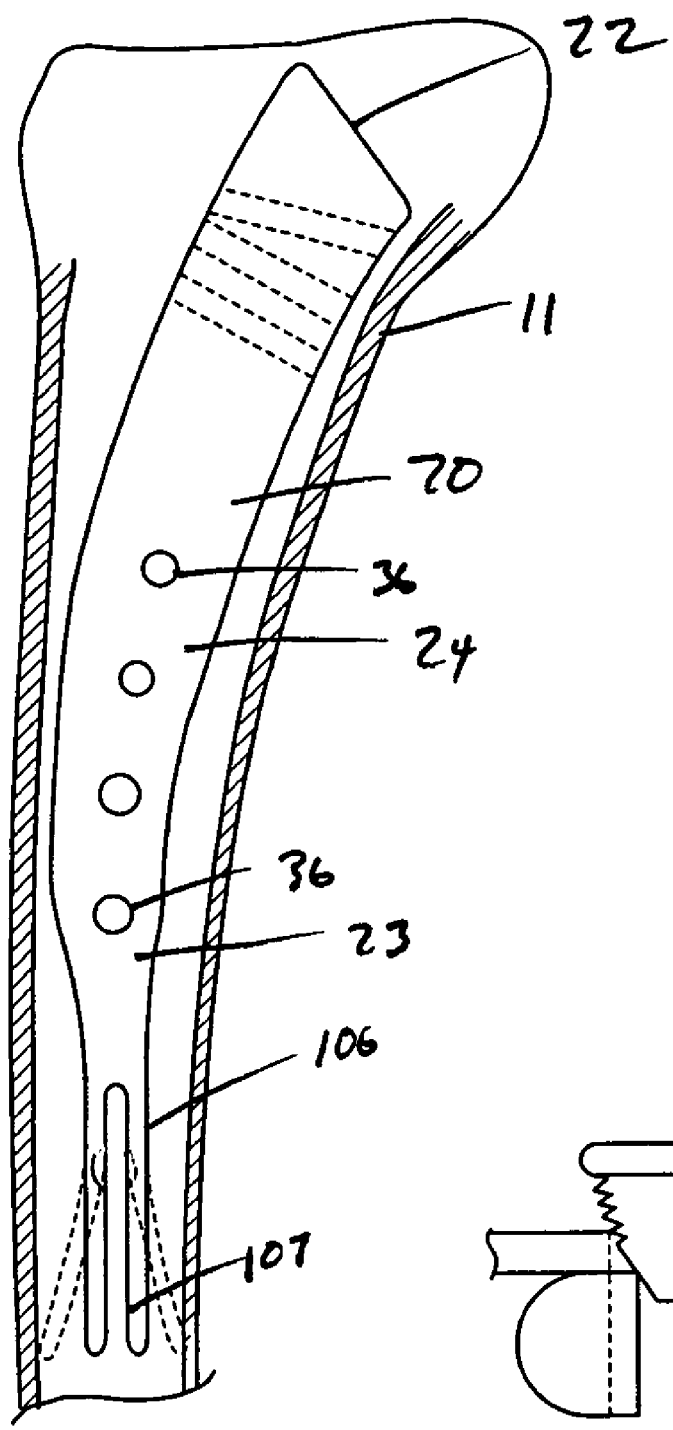
Figure 61:
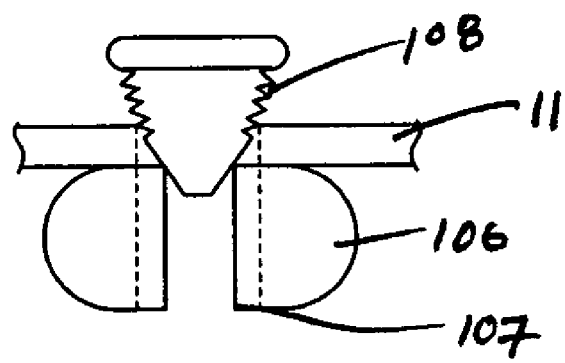
Figure 62:
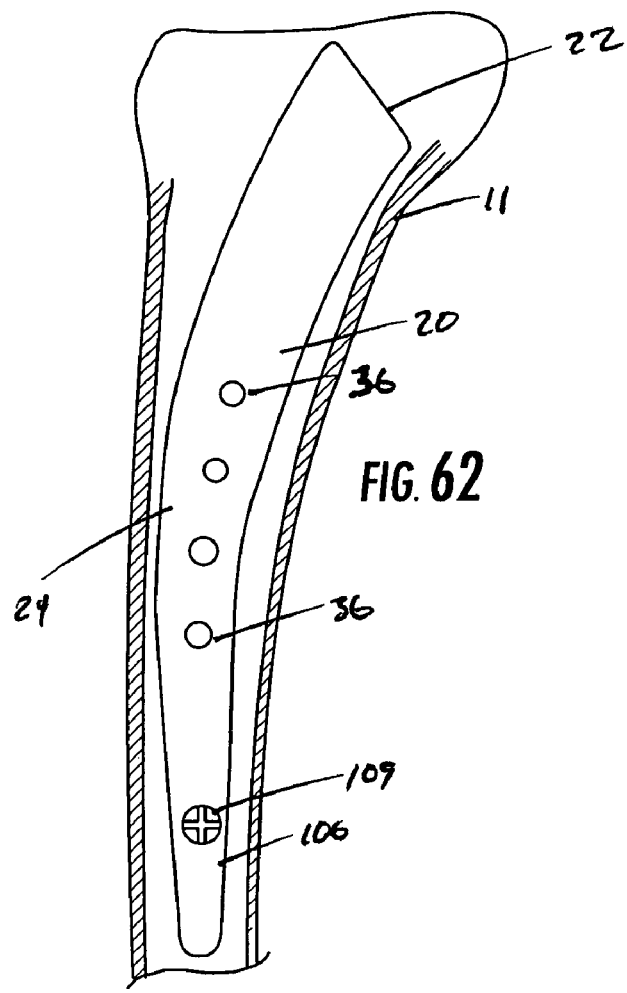
Figure 63:
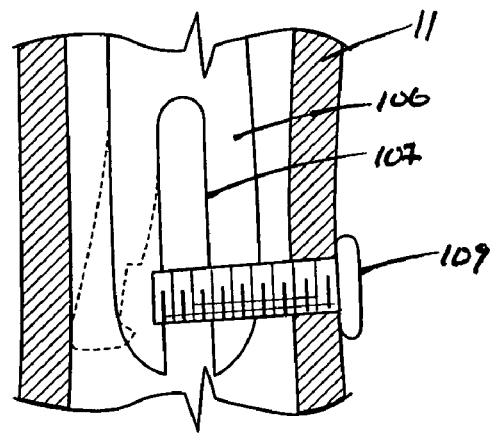
Figure 64:
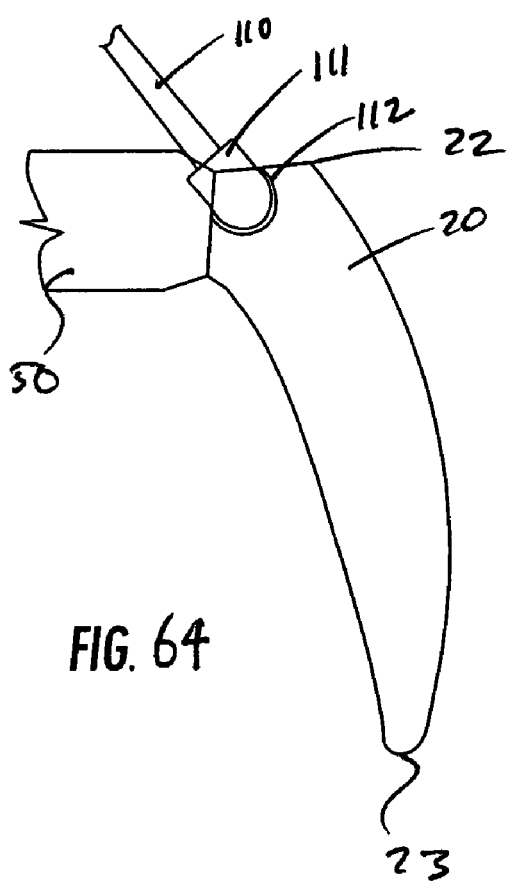
Figure 65:
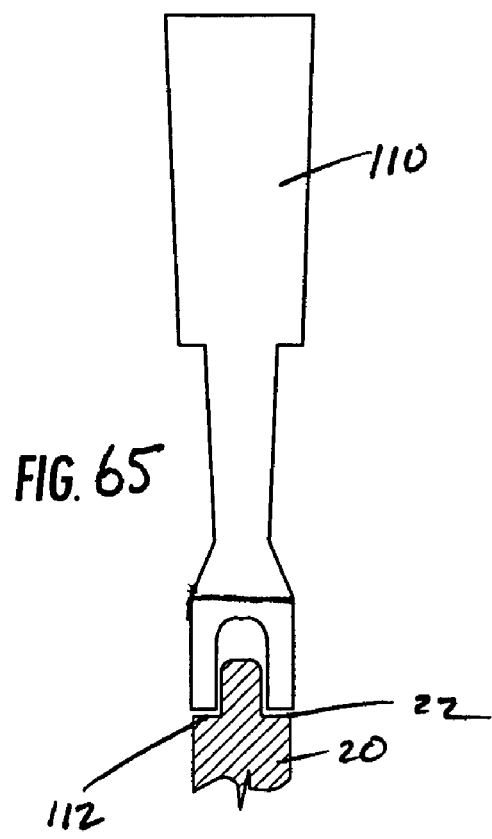
Figure 66:
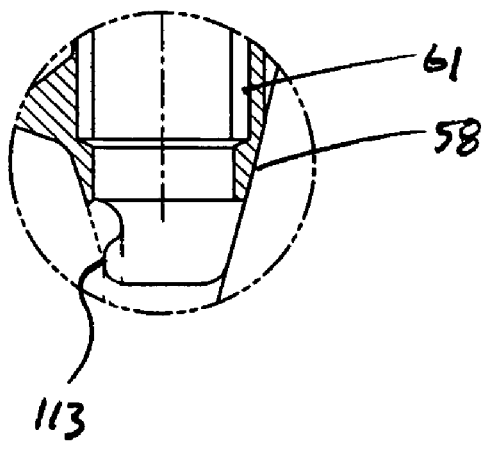
Figure 67:
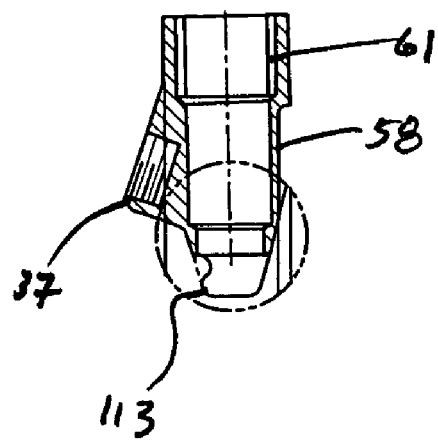
Figure 73:
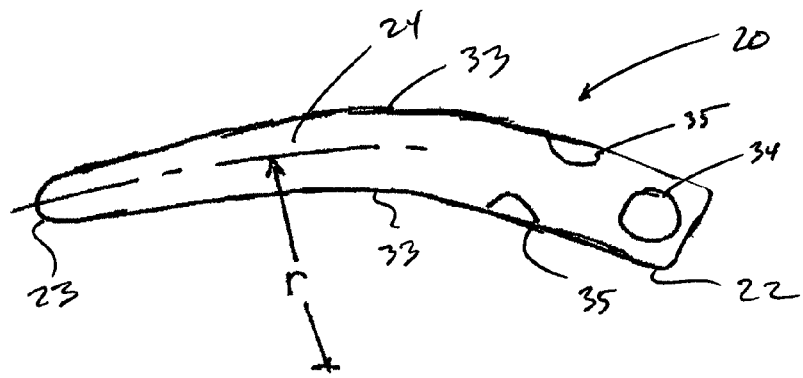
Figure 74:
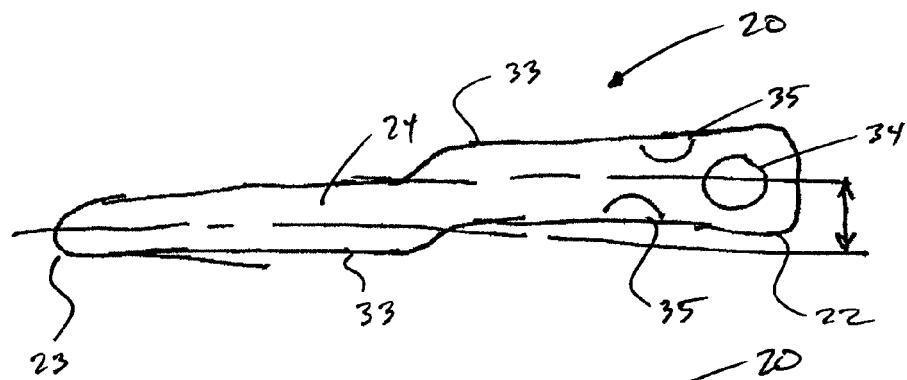
Figure 75:
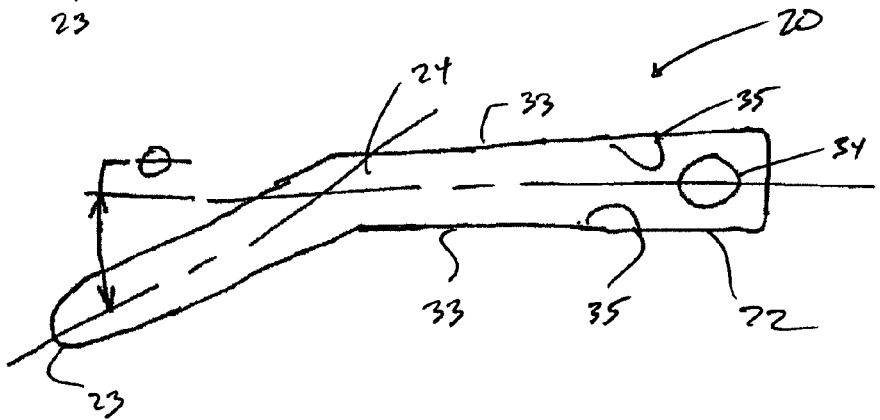

FIG. 7 is a sectional view of the fixation member of FIG. 6;
FIG. 8 is a sectional view of the fixation member of FIG. 6;
FIG. 9 is a sectional view of the fixation member of FIG. 6;
FIG. 10 is a sectional view of the fixation member of FIG. 6;

FIG. 11 is a sectional view of a portion of the fixation member and a pair of bone fasteners of the intramedullary fixation assembly of FIG. 1;

FIG. 12 is a sectional view of one of the bone fasteners shown in FIG. 11;

FIG. 13 is a side elevation view of a fixation member of another embodiment of the present invention, including a stem extending from one of its ends;

FIG. 14 is another side elevation view of the fixation member of FIG. 13;

FIG. 15 is a plan view of a head end of one of the bone fasteners shown in FIG. 11;

FIG. 16 is a side elevation view of the bone fastener shown in FIG. 15;

FIG. 17 is a sectional view of the bone fastener shown in FIG. 15;

FIG. 18 is a plan view of a head of a k-wire for use as a bone fastener in another embodiment of an intramedullary fixation assembly of the present invention;

FIG. 19 is a sectional view of the k-wire shown in FIG. 18;

FIG. 20 is a side elevation view of an outrigger frame of a guide assembly of another embodiment of the present invention shown in FIG. 53;

FIG. 21 is a plan view of the outrigger frame of FIG. 20;

FIG. 22 is another side elevation view of the outrigger frame of FIG. 20;

FIG. 23 is plan view of a targeting guide of the guide assembly of the present invention shown in FIG. 53;

FIG. 24 is a side elevation view of the targeting guide of FIG. 23;

FIG. 25 is another plan view of the targeting guide of FIG. 23;

FIG. 26 is a sectional view of the targeting guide of FIG. 25;

FIGS. 27-30 are various views of the targeting guide of another embodiment of the present invention;

FIG. 31 is a side elevation view of a screw-in drill guide which is part of the outrigger frame of FIG. 20;

FIG. 32 is a sectional view of the screw-in drill guide of FIG. 31;

FIG. 33 is a side elevation view of a drill guide of another embodiment of the present invention;

FIG. 34 is a sectional view of the drill guide of FIG. 33;

FIG. 35 is a side elevation view of a screw guide of a guide assembly as shown in FIG. 59;

FIG. 36 is a sectional view of the screw guide of FIG. 35;

FIG. 37 is a side elevation view of guide member of the outrigger frame shown in FIG. 20;

FIG. 38 is a sectional view of the guide member of FIG. 37;

FIGS. 39 and 40 show a perspective view of attachment of a set of four prongs on the guide member of FIG. 37 within a set of four recesses defined in an end of the fixation member shown in FIG. 6;

FIG. 41 is an enlarged view of the prongs and recesses of FIG. 39 forming an interference fit;

FIGS. 42 and 43 show a side elevation view of a fastener driving drill bit of another embodiment of the present invention;

FIG. 44 is a side elevation of a drill bit of another embodiment of the present invention;

FIG. 45 is a plan view of a hand driver of another embodiment of the present invention;

FIG. 46 is a side elevation view of the hand driver of FIG. 45;

FIG. 47 is a sectional view of a cannulated drill bit of another embodiment of the present invention;

FIG. 48 is a side elevation view of a trialing broach assembly of another embodiment of the present invention;

FIG. 49 is a side elevation of a handle of the trialing broach assembly shown in FIG. 48;

FIG. 50 is a side elevation view of a depth indicator of another embodiment of the present invention;

FIG. 51 is a sectional view of the depth indicator of FIG. 50;

FIG. 52 is a perspective view of the trialing broach assembly of FIG. 48 show inserted into a long bone;

FIG. 53 is a perspective view of the fixation member of FIG. 3 connected to the guide assembly of the present invention;

FIG. 54 is a perspective view of the fixation member and guide assembly of FIG. 53, wherein the fixation member has been positioned in the medullary canal of the fractured long bone;

FIG. 55 is a perspective view of the guide assembly and fixation member shown in FIG. 54, wherein the guide assembly is guiding drilling through an opening in the fixation member and into the long bone;

FIG. 56 is a perspective view of the guide assembly and fixation member shown in FIG. 54, wherein drilling is being guided through another opening in the fixation member;

FIG. 57 is a perspective view of the guide assembly and fixation member of FIG. 54 guiding placement of a bone fastener, such as the bone fasteners shown in FIGS. 11 and 12, through the bone and the opening in the fixation member;

FIG. 58 is a perspective view of placement of another bone fastener using the assemblies of FIG. 57;

FIG. 59 is a perspective view of placement of yet another bone fastener using the assemblies of FIG. 57;

FIG. 60 is a sectional view of a long bone and a fixation member of another embodiment of the present invention, wherein the fixation member includes a split tail;

FIG. 61 is a sectional view of a bone fastener of another embodiment of the present invention positioned within the split tail of the fixation member of FIG. 60;

FIG. 62 is a sectional view of a long bone and a fixation member of another embodiment of the present invention, wherein the fixation member includes a split tail;

FIG. 63 is a sectional view of the long bone and fixation member of FIG. 62 wherein one arm of the split tail is threaded to allow splaying of the split tail FIG. 64 is a side elevation view of an impactor having a U-shaped end and fixation member defining U-shaped slots for receiving the end of the impactor in another embodiment of the present invention;

FIG. 65 is a sectional view of the U-shaped impactor and slot of FIG. 64;

FIGS. 66-72 show assorted views of an S-shaped, positive fit connection between a guide assembly and fixation member of another embodiment of the present invention;

FIG. 73 is a side elevation view of a fixation member of another embodiment of the present invention having a bow tilt;

FIG. 74 is a side elevation view of a fixation member of another embodiment of the present invention having a linear offset; and FIG. 75 is a side elevation view of a fixation member of another embodiment of the present invention having an angular bend.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Figure 2:
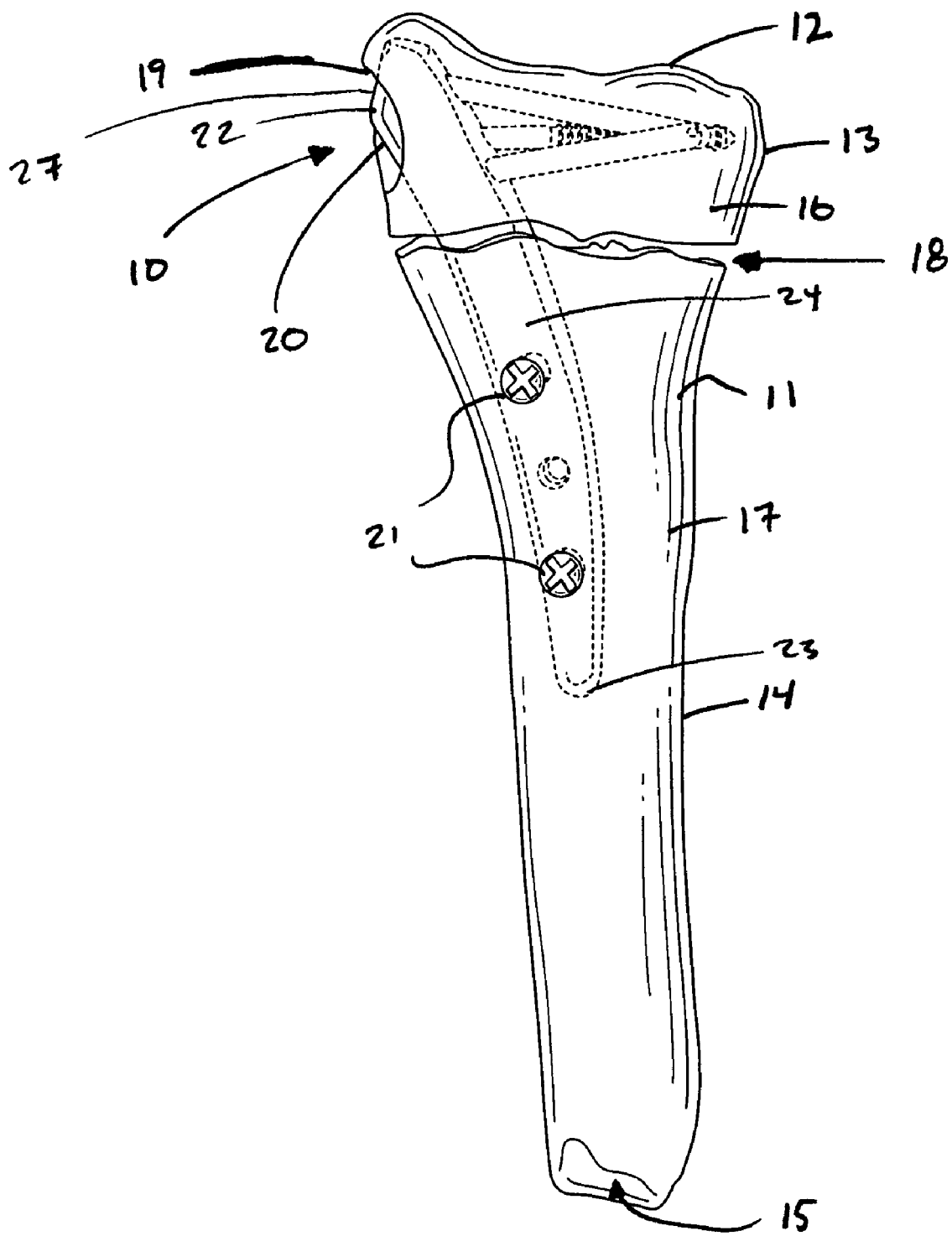
FIG. 2 is an elevation view of the long bone fracture and intramedullary fixation assembly of FIG. 1.

An intramedullary fixation assembly 10 of one embodiment of the present invention is shown installed in a long bone 11 of a patient in FIGS. 1 and 2. The long bone could be any of a number of long bones, such as a femur, tibia, radius or humerus. The fixation assembly 10 is most suited to repairing fractures of the long bone 11 wherein the fracture is at one end near an articular cartilage surface 12 and wherein it is desired to leave the articular surface undisrupted during the repair. Also, the long bone includes a widened end 13 that supports the articular cartilage surface which tapers to a more narrow shaft 14. Extending within the shaft 14 and a portion of the widened end 13 is a medullary canal 15. Generally, every type of long bone will have the afore-described characteristics, such as the shaft 14 being relatively narrower than the end 13. However, the proportional geometry of the different long bones will vary due to their biology and function.

When referred to herein, the terms "different long bones," "various long bones," and other, related terms, do not refer to the same type of long bone in different people, but different types of long bones, such as a femur versus a tibia, or radius, or humerus. In addition, the intramedullary fixation assembly could be used to repair somewhat more complex fractures, but is shown being used to repair a first bone fragment 16 separated from a second bone fragment 17 by a single fracture line 18. A side aperture 19 is defined in a lateral surface of the widened end 13, subjacent the articular cartilage surface 12, to allow insertion of the intramedullary fixation assembly 10.

Generally, the intramedullary fixation assembly 10 includes an elongate fixation member 20 and a plurality of fasteners 21 that extend through the elongate fixation member to attach it to the long bone 11 above and below the fracture line 18 and thereby reduce the fracture, for example as shown in FIGS. 1 and 2. The elongate fixation member 20 preferably, when positioned within the medullary canal 15 of the long bone 11 (regardless of its type), has a first end 22 positioned adjacent the side aperture 19. Extending from the first end, through the rest of the aperture and into the medullary canal 15 of the first bone fragment 16, is a curved body 24 (shown in broken lines in FIGS. 1 and 2) of the fixation member 20. The curved body 24 extends to a second end 23 which is positioned within the medullary canal 15 of the second bone fragment 17. Advantageously, a radius of curvature of the curved body 24 is selected to promote smooth insertion of the curved body through the side aperture 19 and into the medullary canal 15 despite differences in the width of the widened end 13 and the shaft 14 and medullary canal 15 between the various types of long bone 11.

For example, one embodiment of the fixation member 20 of the present invention is shown in FIGS. 3-14. The first end 22 of the fixation member 20 has two intersecting flat surfaces, including an exposed first end surface 27 that is accessible through the side aperture 19 and an adjacent first end surface 28 that is at a right angle to the exposed surface, as shown in FIG. 4. The second end 23 of the fixation member 20 has a rounded profile with a radius of about 0.08 inches, as shown in FIG. 4, and edges rounded to about a 0.06 inch radius, as shown in FIG. 5.

The curved body 24 of the fixation member 20 includes a convex side 29 and a concave side 30 that are on opposite sides of the curved body. The sides have radii of curvature with a similar center, but the center of the convex side changes so that the sides converge in a slight taper as they extend to the second end 23, as shown in FIG. 4. For instance, the radius of curvature of the concave side 30 is about 3.12 inches and the radius of curvature of the convex side 29 is about 3.36 inches near the first end 22 when measured from a first center 31 positioned about 2.14 inches from the plane of the adjacent first end surface 28 and about 2.47 inches from the plane of the exposed first end surface 27. But, the radius of curvature of the convex side 29 shifts to about 2.68 inches at a second center 32 that is positioned about 1.89 inches from the plane of the adjacent first end surface 28 and about 1.5 inches from the plane of the exposed first end surface 27.

Notably, this shift produces the taper near the second end 23 of the fixation member 20. Also notable is that maintaining a constant radius of curvature near the first end 22 of the curved body 24 allows for different sized and different types of long bones to be accommodated merely by extending the arc further to produce a greater "hook." This overcomes the increase in not only the length of the long bone 11, but also the increase in distance between widened end 13 and width of the medullary canal 15, facilitating its use on different and larger types of long bones. If measured from the centerline of the curved body 24, the radius of curvature can actually be constant between the sides 29, 30 and the ends 22, 23 regardless of the amount of taper. This radius of curvature can also be maintained while the arc length of the curved body 24 is extended to account for increased length of the long bone 11 and increased offset between the side aperture 19 and the position of the medullary canal 15. As a result, an entire kit of fixation members could have the same radius of curvature but be usable in different types and lengths of long bones.

A second pair of opposite, side surfaces 33 extend between the convex side 29 and concave side 30, as shown in FIGS. 3 and 5. Similar to the convex side 29 and concave side 30, the side surfaces 33 taper slightly toward each other as they extend from the first end 22 to the second end 23 of the curved body 24. However, the side surfaces 33 in the illustrated embodiment are relatively planar, as opposed to the curved shape of the sides 29, 30. Advantageously, the taper of the sides 29, 30, 33, the continuous curve of the curved body 24 between the ends 22, 23 and the rounded profile of the second end 23 help to facilitate insertion through the side aperture 19 and into the medullary canal 15. Note that the term "continuous" differs from "constant" in reference to curvature herein in that a continuous curvature is not necessarily a constant curvature. In addition, the use of radii of curvature within about the ranges cited above, with variations of about 1.5 to 5 inches, allow the fixation member 20 to be employed in different (preferably human) long bones with only variations in the overall length of the fixation member.

There may be some adaptations of the fixation member 20 beyond extension of the arc length, such as through the application of a tilt. The tilt would generally not be in the curvature defined by the convex and concave sides 29, 30 to accommodate curvature in different long bones. For example, a volar tilt may be used to accommodate the volar tilt in the saggital plane of the human radius. In this instance, volar tilt facilitates better filling of the medullary canal of the distal radius and can improve stabilization of the fixation member 20. Generally, the tilt can be accomplished, for example, through the use of a radial bow, as shown in FIG. 73, a linear offset, as shown in FIG. 74, or an angular bend, as shown in FIG. 75. The radial bow ranges from about 4 to 8 inches (100 to 200 mm) of curvature. The linear offset is about 2 to 5 mm and the angular bend is about a 10° to 20° angle.

To allow passage of the fasteners 21 through the fixation member, a plurality of fastener openings are defined in the fixation member. These fastener openings include a side aperture accessible fastener opening 34, a pair of fastener openings 35 extending between the curved convex side 29 and concave side 30, and fastener openings 36 extending between the side surfaces 33. The fastener opening 34 extends from the exposed first end surface 27 (which is accessible through the side aperture 19 when the fixation member 20 is installed) through a portion of the curved body 24 and to the convex side 29, as shown in FIGS. 4 and 5. The fastener opening 34 includes a guide portion 38 and a fastener head portion 39 that is generally more narrow than the guide portion. Both of the portions are threaded, as shown in FIGS. 7 and 8, to facilitate a secure fit by the fasteners 21 and various installation devices, as will be described in more detail below. Defined around the periphery of the guide portion 38 of the fastener opening 34 are four concave channels, recesses or indentations 40. These indentations are arranged in a cross, or cruciform, shape each radiating out from the fastener opening 34 and spaced 90° from each other. As will be described in more detail below, the concave indentations 40 serve to provide for a secure, positive fit with a guide assembly 50.

The pair of fastener openings 35 which extend between the sides 29, 30 extend through the curved body 24 nearer the first end 22 so as to be within the first bone fragment 16, as shown in FIG. 5. Each of the fastener openings also has a threaded fastener portion 39 similar to the fastener opening 34, but a non-threaded guide portion 38, as shown in FIGS. 9 and 10. These fastener openings 35 extend at different, divergent angles than each other and the orientation of the fastener opening 34 which is relatively orthogonal with respect to the exposed first end surface 27 and the convex side 29, as shown in FIG. 3. As a result, the fastener openings of the present invention (such as the fastener openings 35) need not all be aligned with the axis of the fixation member.

These different angles improve fixation by allowing angled insertion of the fasteners into different portions of the first bone fragment 16, as shown in FIGS. 1 and 2. In addition, the angles of the fastener openings 34, 35 may be configured so that the fasteners extend subjacent to the articular cartilage for improved fixation. Generally, this will require the fastener openings 34, 35 to extend at some acute angle, such as an angle between about 50° and 85° (depending on the origin of the fastener opening), and preferably about 60° to 70°, with respect to the fixation member body. Basically, these angles are to match the inclination angle of the articular surface so as to provide a buttress effect for the articular cartilage. For instance, the ulnar inclination angle of the articular cartilage on the radius is about 23° (resulting in a 67° fastener opening angle). The buttress effect is also improved by the sub-chondral placement of the first end surface 28 that is adjacent and at a right angle with respect to the exposed first end surface 27 so as to underlie the articular cartilage.

In the illustrated embodiment shown in FIGS. 4 and 6, three fastener openings 36 are defined in the curved body 24 at a position nearer the second end 23 of the fixation member 20. The two outer ones of the fastener openings 36 are configured to receive threaded fasteners 21, similar to the fastener openings 34, 35, but the center one of the fastener openings 36 is configured to receive a relatively smaller diameter k-wire fastener 41, as shown in FIG. 6. Preferably, the larger of the fastener openings 36 are not threaded to allow a slip fit of the threaded fasteners 21 without damaging the threads, as will be described below.

The threaded fasteners 21 are shown in greater detail by FIGS. 15-17 and the k-wire fastener 41 by FIGS. 18 and 19. Each of the fasteners 21, 41 is shown as being driven by a Phillips-type, or cruciform-type, head (FIGS. 15, 17 and 18), but may be configured for mating with a driver in any number of ways, such as with an Allan-type head or flat head. Each of the illustrated threaded fasteners 21 includes a head 42, a threaded shaft 43, a non-threaded shaft portion 45 and a bone-securing end 44, as shown in FIG. 16. The head 42 of each of the threaded fasteners 21 has a larger diameter than its shaft 43, so as to prevent the threaded fastener from passing through tapped openings in the first layer of cortical bone. However, the diameter of the head 42 is still small enough to pass through a screw guide 51, or other guide, positioned by the guide assembly 50 within the guide portion 38, as will be described in more detail below.

When the threaded fasteners 21 are inserted through the openings 34, 35 and into the first bone fragment 16, the head is configured to reside in the guide portion 38, the threaded shaft 43 in the threaded fastener portion 39 and the bone-securing layer is configured to attach to the distant layer of cortical bone opposite the side aperture 19 and subjacent the articular cartilage surface 12, as shown in FIGS. 1 and 2. When inserted through the openings 36 and into the second bone fragment 17, the threaded shaft 43 is configured to attach to the first layer of cortical bone, the non-threaded shaft portion 45 is configured to reside in the openings 36 in a slip fit and the bone-securing end 44 is configured to attach to the distant layer of cortical bone opposite the first layer of cortical bone, as shown in FIG. 11. The fastener head 42 is configured to abut the first layer of cortical bone, and may have a rounded shape to minimize irritation of the overlying tissues, as shown in FIG. 12. Notably, when used in the openings 36, the threaded fasteners 21 become bi-cortical screws, firmly attaching to two layers of cortical bone. As another option, the non-threaded shaft 45 may include a chamfer 63 to help locate the screw in the openings 36 as it is advanced through the fixation member 20.

The bone-securing end 44 preferably has threads and an outer diameter that is smaller than the minimum, trough diameter of the threads on the threaded shaft 43 and the diameter of the un-threaded shaft portion to prevent the bone-securing end from locking up or fretting the threads when passing through the fastener portion 39. A neck 46 on each of the threaded fasteners 21 also prevents lockup by providing space between the threaded fastener shaft 43 and fastener head 42, as shown in FIGS. 16 and 17. As shown in FIG. 19, the k-wire fastener 41 also includes a fastener head 42, a neck 46, a threaded shaft 43 and a non-threaded shaft portion 45, but its bone securing end 44 is not threaded for easier insertion as the first fastener.

During installation, the threaded shaft 43 of one of the threaded or k-wire fasteners 21, 41 mates with the threaded fastener portion 39 of its respective one of the fastener openings 34, 35 and 36 and the bone-securing end 44 extends into the long bone 11 for a secure fit, as shown in FIGS. 1 and 2. It should be noted that although two types of fasteners are described herein that are preferred, other types of fasteners may also be employed, including other types of wires, screws, etc., and still be within the purview of the present invention as long as some portion of the fastener secures itself to the fixation member 20 and another portion to the long bone 11.

FIGS. 20-30 illustrate the guide assembly 50 of the present invention that is used to position the screw guide 51, a screw-in drill guide 52 and a plurality of other drill guides 53, shown in FIGS. 31-36. The guide assembly 50 includes an outrigger frame 54 having a curved, hook-shaped body 55 including a first end 56 for positioning fasteners 21 within the first end 22 of the fixation member 20 and the first bone fragment 16, and a second end 57 for positioning fasteners within the second end 23 of the fixation member and the second bone fragment 17, as shown in FIGS. 20-22.

The outrigger frame 54 also includes a guide member 58 that has a truncated pyramid shape and extends from a flat surface of the first end 56 of the hook-shaped body 55, as shown in FIGS. 20 and 22. The guide member 58 tapers as it extends outward from the hook-shaped body and ends in four prongs 59, as shown in FIGS. 37-40. Each of the prongs 59 has a rounded shape with opposing edge surfaces 60 angled toward each other (i.e., they are generally converging) as they extend outwards from the end of the truncated pyramid shape. These converging surfaces are spaced so as to fit into similarly shaped, but somewhat smaller, concave indentations 40 in a positive, or interference, type fit, as shown in FIGS. 39-41. The guide member 58 and its subjacent portion of the hook-shaped body 55 define a stepped opening 61, as shown in FIG. 38, that is sized to receive the screw-in drill guide 52 (shown in FIGS. 31 and 32). The stepped opening 61 includes shoulders 62 that prevent the passage of the screw-in drill guide 52.

The screw-in drill guide 52 includes a burled knob 65, an elongate shaft 66, a tapered shoulder 67 and a threaded tip 68. The burled knob provides 65 a gripping surface for tightening the screw-in drill guide 52 and its relatively large diameter acts as a stop against passage of the screw-in drill guide through the stepped opening 61 when inserted therein and tightened. The elongate shaft 66 extends from the burled knob and tapers at the tapered shoulder 67 down to the diameter of the threaded tip 68. This shape allows passage of the threaded tip through and out of the stepped opening 61 so that the threaded tip 68 can be advanced into the threads of the guide portion 38 of the fastener opening 34. Defined within the screw-in drill guide 52 is a guide opening that extends from the burled knob 52 through to the threaded tip 68 and includes a large diameter portion 70 that tapers to a small diameter portion 71 near the threaded tip, as shown in FIG. 32. This change in diameter helps to concentrically center the fasteners 21 as they are advanced through the screw-in drill guide 52 and into the fastener opening 34 defined in the fixation member 20, as will be described below.

When the threaded tip is advanced into the threads of the guide portion 38, the guide member 58 and its prongs 59, which are also spaced in a cruciform or cross pattern similar to the indentations 40, are advanced into the indentations, as shown in FIG. 40. The cruciform pattern, combined with the positive fit, firmly locks the outrigger frame 54 to the fixation member 20 before and during guidance of insertion of the various fasteners 21, 41. This firm attachment guards against relative motion of the guide assembly 50 with respect to the fixation member 20, so that misalignment of the guides 51, 52, 53 is reduced even with just a single point of attachment of the guide assembly to the fixation member.

The cruciform shape and positive fit are particularly effective at restricting rotation between the guide assembly and fixation member, which can be a problem due to the relative length and cantilevered configuration of the guide assembly and fixation member, especially on the larger long bones such as the tibia and femur. It should be noted, however, that the positive fit of the prongs 59 in the concave indentations 40 could be accomplished in other ways, such as by having the indentations on the guide member 58 instead of the exposed first end surface 27 of the fixation member 20.

In addition, different numbers and configurations of the prong and indentation arrangement are also possible to achieve a firm positive fit, even though the cruciform arrangement is preferred for reducing rotational motion. For instance, the positive or press fit may be implemented or facilitated, as shown for example in FIG. 41, by slightly over-sizing a male fitting portion (e.g., the prongs 59) with respect to a female portion (e.g., the concave indentations 40) so that the angled opposing surfaces (e.g., converging edge surfaces 60) are in contact and the tip of the male portion, and other remaining flat surfaces have minimal contact to allow the angled surfaces to wedge into each other.

Returning to a discussion of the first end 56 of the hook-shaped body 55 of the outrigger frame 54, the first end 56 further supports two screw guides 51 that are integrally connected to, and extend from, the first end of the hook-shaped body, as shown in FIGS. 20-22. These screw guides 51 are cylindrical tubes that define openings extending therethrough and are oriented so as to have an axis collinear and aligned with the axes of the of the pair of openings 35 defined in the curved body 24 of the fixation member 20. Preferably, the screw guides 51 are oriented so that the fasteners 21 extend at an angle into the first bone fragment 16 right below the articular cartilage surface 12, as shown in FIGS. 1 and 2. In addition to the screw guides 51, the first end 56 also includes a handle mount 37 defining a threaded opening.

Referring now to the second end 57 of the hook-shaped body 55, there is supported a channel member 72 of the outrigger frame 54 that extends away from the second end of the hook-shaped body. The channel member 72 has an elongate rectangular shape, as shown by FIGS. 21 and 22, and includes a pair of channel arms 73 extending away and along the length of the rectangular shape, as shown in FIGS. 20 and 21. Each of the arms defines an angled surface 74 extending toward the other one of the arms and the arms are spaced from each other and parallel so as to define a channel. Extending into the channel defined between the arms 73 is a stop 75. In addition, the second end 57 and the channel member 72 define a locking member opening 76 that extends into the channel between the arms 73. The locking member opening 76 is sized and includes threads to receive advancement of a locking member 77, as shown in FIGS. 20 and 22. The locking member includes its own burled knob 78 to facilitate its advancement and also has a frusto-conical shaped distal locking tip 79 that extends out of the locking member opening 76 and into the channel between the arms 73 when the locking member 77 is fully advanced, as shown in FIGS. 20 and 21.

Also included in the guide assembly 50 is a targeting guide 80 (as shown in FIGS. 23-26) that is configured to support and orient the drill guides 53 and screw guides 51 that are used to guide insertion of the fasteners 21, 41 through the fixation member 20 and into the long bone 11. Different targeting guides 80 can also be used for different sized fixation members 20 (e.g., as shown in FIGS. 27-30), and can be employed in right and left handed configurations depending on the type of long bone being treated and the orientation of the side aperture 19. The targeting guide includes a guide portion 81 and a slide attachment portion 82. The guide portion 81 defines a plurality of guide openings 83 sized for the passage of screw guides 51 or drill guides 53 sized for threaded fasteners 21 or for the smaller diameter k-wire fasteners 41. The guide openings 83 are positioned along an arc (as shown in FIGS. 23 and 25) to correspond to the placement of the openings 36 through the side surfaces 33 of the curved body 24 so as to guide the fasteners 21, 41 into the openings 36. Optionally, one of the smaller diameter openings 83 may be placed to orient insertion of one of the k-wire fasteners 41 external to the fixation member 20 to avoid additional holes in the fixation member and provide for temporary securing of the guide assembly 50.

The slide attachment portion 82 is generally rectangular and defines a pair of slots 84 that extend to one edge of the side attachment portion. As is shown in FIG. 26, these slots are defined by a pair of angled, opposing surfaces 85. In addition, at about a midpoint along one edge of the slide attachment portion 82 is defined a circular centering divot 86 with sloped sides, as shown in FIGS. 24 and 26. During attachment of the targeting guide 80 to the channel member 72, the pair of slots 84 of the slide attachment portion 82 are inserted between the channel arms 73 until approximately at the end of travel of the slots. Then, the locking member 77 is advanced in the opening 76 until the locking tip 79 enters the centering divot 86. The sloped sides of the centering divot 86 interact with the sloped edges of the locking tip 79 which forces the targeting guide 80 to center and forms a relatively tight, positive fit. Once the locking tip 79 bottoms within the centering divot 86, further advancement of the locking tip pushes the angled, opposing surfaces 85 of the slots against the angled surfaces 74 of the channel arms 73. This also has the effect of centering the targeting guide 80 between the channel arms 73 and also forms a relatively tight, positive fit. In this manner, a positive fit is used once again to ensure tight assembly of the parts and accurate guidance for the insertion of various fasteners 21, 41.

As shown in FIGS. 33-36, each of the screw and drill guides 51, 53 include a grip flange 48 at one end of an elongate shaft 49 that defines teeth 47 at its other end. Defined within the elongate shaft 49 of the drill guide is a guide shaft opening that tapers from a wider to narrower diameter near the teeth 47, as shown in FIG. 34. This corresponds with the dual diameter drill bit 90 shown in FIG. 44, wherein the larger diameter of the drill bit prevents travel of the drill bit beyond the shoulder defined within the shaft 49 of the drill guide 53 so as to prevent drilling past a selected depth for safety. The elongate shaft 49 of the screw guide 51 also defines a guide shaft, but this guide shaft has a constant diameter because, as described above, the fasteners 21, 41 are restrained by the structure of the fixation member 20 from advancing too far.

During use the drill guides 53 are first inserted into the guide openings 83 of the guide portion 81 of the targeting guide and are advanced until the teeth 47 contact skin or bone (so as to prevent rotation of the guides). A pilot hole is drilled using the drill bit 90 guided by the drill guides 53. Then, the drill guides 53 are removed and screw guides 51 are inserted in the guide openings 83 until the teeth 47 contact skin or bone. The selected one of the threaded or k-wire fasteners 21, 41 are advanced at the end of a driver 91 (as shown in FIGS. 42 and 43) until penetrating the fixation member 20 through one of the openings 36 and into the long bone 11 (in this case the second bone fragment 17). The driver 91 or drill bit 90 may be advanced using power or by hand, such as by a hand driver 92, as shown in FIGS. 45 and 46.

During installation of the intramedullary fixation assembly 10, a k-wire is inserted into a lateral side of the widened end 13 of the long bone 11 subjacent the articular cartilage surface 12 and used to guide a cannulated drill bit 94, as shown in FIG. 47. The cannulated drill bit clears the side aperture 19 and a conventional bone awl (not shown) is used to open the medullary canal 15 of cancellous bone.

A trialing broach 95, as shown in FIGS. 48 and 52, is pushed, twisted, hammered, etc., into the long bone 11 through the side aperture 19 to approximate the size of the fixation member 20. The trialing broach includes a handle 98 and an awl point 99. The handle 98 includes a head 100 that facilitates gripping and hammering at one end and a threaded connector 101 at the other end, as shown in FIG. 49. This threaded connector is similar to the threaded tip 68 of the screw-in drill guide allowing the exchange of the awl point 99 with other awl points of different sizes, each having threaded opening at one end similar to the threaded opening 34 on the fixation member 20. Preferably, the awl point 99 has some type of teeth or cutter (as shown symbolically by the cross-hatch pattern 96) to aid in bone removal and sizing.

Advantageously, the trialing broaches 95 may eliminate the need for many awls and cutting tools. However, other conventional tools, such as reamers and awls could also be employed to clear bone. Each of the broaches 95 may also include a depth indicator, such as the notch 97 shown in FIG. 48, that indicates the correct depth for that size of fixation member 20. The depth indicator or notch 97 may include the use of fluorescent paint so as to be easily visually detectable.

Once the side aperture 19 has been formed and the medullary canal 15 cleared and sized, an appropriately sized fixation member 20 is selected based on the various above-described measurements. The handle 98 of the trialing broach 95 is removed from the awl point 99 and attached to the threaded opening defined in the handle mount 37 via the threaded connector 101 on the handle, as shown in FIG. 53. Then, the outrigger frame 54 of the guide assembly 50 is attached to the fixation member. In particular, the screw-in drill guide 52 is extended through the stepped opening 61 of the guide member 58 and its threaded tip 68 is advanced into the threaded opening 34 of the guide assembly. This assembly mates the prongs 59 with the concave indentations 40, thereby locking out micro-motion and rotation between the outrigger frame 54 and the fixation member 20, as shown in FIGS. 39 and 40.

After fixation of the outrigger frame 54, the targeting guide 80 is attached to the channel member 72 by sliding the channel arms 73 within the pair of slots 84 on the guide portion 81 until the targeting guide is against the stop 75. Then, the locking member 77 is advanced in the opening 76 until the locking tip 79 enters the centering divot 86. The sloped sides of the centering divot 86 interact with the sloped edges of the locking tip 79 which forces the targeting guide 80 to center and forms a relatively tight, positive fit. Once the locking tip 79 bottoms within the centering divot 86, further advancement of the locking tip pushes the angled, opposing surfaces 85 of the slots against the angled surfaces 74 of the channel arms 73.

The handle 98 and guide assembly 50 are then used to slide the fixation member 20, as facilitated by the tapered ends 22, 23 through the side aperture 19 and into the medullary canal 15, as shown in FIG. 54. The handle 98 is then unscrewed from the handle mount 37. As an option, the fixation member 20 may include radio-lucent targeting indicia to aid in positioning of the fixation member and guide assembly 50. The length of the handle 98 allows for easy readjustment of the position of the fixation member 20.

Smaller guide openings 83 on the targeting guide 80 are used to place a temporary k-wire fastener 41, such as by using the smaller opening falling outside of the fixation member 20. This allows for a temporary fixation into both the first and second bone fragments 16, 17. The drill guides 53 are placed into the appropriately sized openings 83. The dual-diameter drill bit 90 is advanced into the drill guides 53, the screw guides 51 connected to the hook-shaped body 55 (if necessary) and the guide member 58 to form pilot holes in the long bone 11, as shown in FIGS. 55 and 56.

The depth of these holes are then tested using a depth gauge 102, as shown in FIGS. 50 and 51. The depth gauge 102 may also employ fluorescent paint to ensure clear readability, such as on measurement numbers and hash marks 103. The depth measurements facilitate selection of fasteners 21, 41 of the appropriate length. If necessary, the drilled holes are then tapped (not shown) to prepare them for insertion of threaded fasteners 21. After tapping, the drill guides 53 are replaced with the screw guides 51 (if necessary) and the threaded fasteners 21 are advanced through the aligned openings 34, 35, 36 in the fixation member 20 and the long bone 11 so as to connect the bone fragments 16, 17, as shown in FIGS. 57, 58 and 59. The guide assembly 50 and handle 98 can then be removed by removal of the temporary k-wire fastener 41 and the screw-in drill guide 52.

In another embodiment of the present invention, the fixation member 20 of the intramedullary fixation assembly 10 may include a tail portion 105 extending from, or as part of, the second end 23, as shown in FIGS. 13 and 14. The tail portion has a much smaller diameter or thickness than the curved body 24 and is relatively straight to conform to the straightness of the shaft 14 of the long bone 11. The tail portion in some circumstances can improve the tightness of fit of the fixation member 20 in the second bone fragment 17 with its extra length. Another option for improving the fit within the second bone fragment is to employ the use of a split tail 106, as shown in FIG. 60. The split tail defines a slot 107 that separates the split tail into two spaced arms that are drawn against the cortical wall and urged apart as a tapered screw 108 is advanced through the slot, as shown in FIG. 61. Alternatively, the slot 107 of the split tail 106 may also be placed in an opposite plane with a threaded opening in one of the arms so that passage of a standard screw therethrough pushes the arms apart for additional stability, as shown in FIGS. 60 and 61. In another embodiment, the split tail portion 105 has a spring bias due to construction from a flexible material, such as a metal material, and wherein the split tail is defined by a coronal slot.

In still another embodiment of the present invention, the fixation member 20 may be shaped to accommodate a driving handle 110 by having defined in its first end 22 a pair of U-shaped slots 112 on either side of the fixation member, as shown in FIGS. 62 and 63. The driving handle 110 includes a horseshoe or U-shaped impact end 111 that straddles the fixation member 20, inserting into the U-shaped slots 112 wherein the rounded shapes avoid eccentric loading while the fixation member is being driven into the medullary canal 15. Clearance may also be defined in the guide assembly 50 for the impact end 111 to allow the guide assembly to remain attached during driving. As another alternative, the slots 112 may also be defined in the guide assembly 50 for driving the fixation member 20 via its attachment to the guide assembly.

Figure 68:
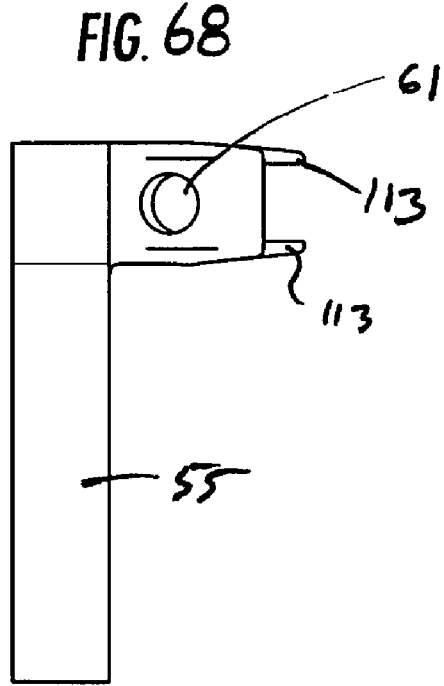
Figure 69:
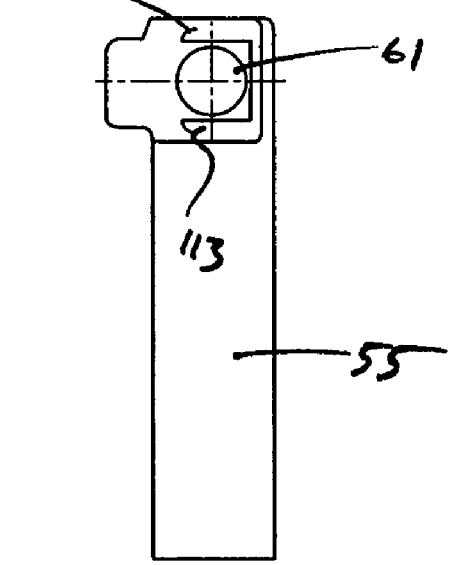
Figure 70:
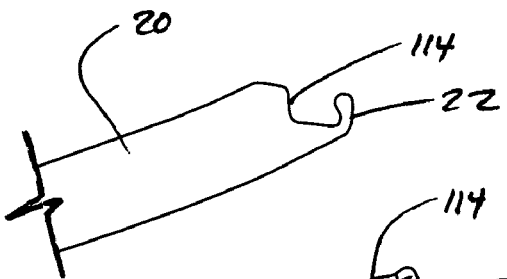
Figure 71:
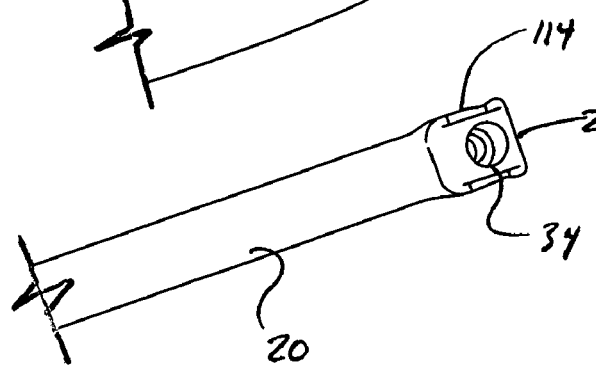
Figure 72:
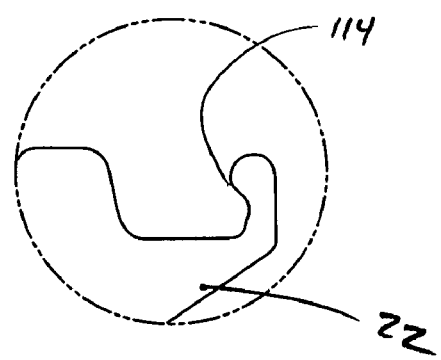

In yet another embodiment of the present invention, in lieu of the afore-described connection between the prongs 59 and the concave indentations 40, the guide member 58 may include a pair of S-curved fittings 113, as shown in FIGS. 64, 65, 66 and 67, that are configured to mate in a positive fit with S-curved slots 114 defined on the first end 22 of the fixation member 20, as shown in FIGS. 68, 69 and 70.

The present invention has many advantages. For example, the invention has many attributes that facilitate its use for different types of human long bone 11 wherein the fixation device extends from the metaphysis to the diaphysis (via the positioning of the side aperture 19), but not through the epiphysis, so as to avoid damaging the articular cartilage. Maintaining a constant radius of curvature near the first end 22 of the curved body 24 allows for different sized long bones to be accommodated merely by extending the arc further to produce a greater "hook." This overcomes the increase in not only the length of the long bone 11, but also the increase in distance between widened end 13 and width of the medullary canal, facilitating its use on different and larger types of long bones. It has also been determined that use of a radius of curvature in the range of 1.5 to 5 inches facilitates use with different types of long bone 11, especially when the curved body 24 curves continuously along its length and the ends 22, 23 are tapered for easy insertion.

The use of a cruciform shape and positive fit or wedge effect used for the concave indentations 40 and the prongs 59 provides rotational and translational stability of the fixation member 20 when attached to the guide assembly 50. In addition, the positive fit or wedge effect operates to center and reduce micro-motion between the targeting guide 80 and the rest of the guide assembly 50. Use of the positive fit of the channel arms 73, the locking tip 79, the slots 84 and the centering divot 86 is capable of achieving an accuracy in the range of one hundredths of an inch. Further, the improved positioning from the positive fit allows the single guide assembly 50 to facilitate placement of all of the fasteners, eliminating the need to use multiple assemblies and select openings via X-rays or other visual or manual method.

Use of k-wire fasteners 41 and k-wire sized guide openings 83 and openings 36 in the curved body 24 of the fixation member 20 allow the fixation member 20 and guide assembly 50 to be temporarily fixed to the long bone 11 after reduction of the fracture. This allows the health care personnel to use both hands to insert the remaining fasteners 21, 41. The cannulated, screw-in drill guide 52 with its internal guide shaft allows for insertion of fasteners 21, 41 into both the first and second bone fragments 16, 17 without removal or reconfiguration of the guide assembly 50. The progressively smaller diameters of the fastener head 42, threaded shaft 43, non-threaded shaft 43 and threaded, bone-securing end 44, and the smoothness of the non-threaded shaft, limit fretting of the threads on the bone-securing end. The stop 75 prevents mounting of a left oriented targeting guide 80 to a left-handed outrigger frame 54 and vice-versa for a right handed outrigger frame. The dual diameters 70, 71 of the drill guides 53 ensure concentricity of the dual-diameter drill bit 90.

Many modifications and other embodiments of the inventions set forth herein will come to mind to one skilled in the art to which these inventions pertain having the benefit of the teachings presented in the foregoing descriptions and the associated drawings. For example, the fixation member 20 may have defined on its outer surface grooves or texture (similar to the awl point 99) that facilitates a tight fit in the medullary canal 15 or can hold biologic or pharmacologic materials to facilitate bone ingrowth. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of repairing a fractured long bone, wherein the long bone includes a medullary canal, said method comprising:
    defining a side aperture in the long bone subjacent cartilage and near an end of the long bone, said side aperture extending into the medullary canal of the long bone;
    attaching a guide attachment member of a guide frame to an end of a fixation member, including;
        mating a pair of opposite, generally converging surfaces defined on the guide attachment member with opposite, generally converging surfaces defined on the end of the fixation member; and
        extending a guide attachment fastener through the guide frame and securing the guide attachment fastener to the fixation member so as to draw the converging surfaces of the guide attachment member and the end of the fixation member together into a positive fit;
    inserting the fixation member through the side aperture until the fixation member is positioned in the medullary canal and side aperture with the guide frame attached thereto; and
    advancing bone fasteners through guide openings defined in the guide frame, the long bone and into openings defined in the fixation member so as to secure fragments of the long bone together, wherein advancing comprises advancing a bone fastener through a guide opening defined in the guide attachment fastener.

2. A method of claim 1, further comprising extending a screw guide into one of the guide openings defined in the guide frame and wherein advancing bone fasteners includes advancing the fasteners through an opening defined in the screw guide.

3. A method of claim 1, wherein advancing the bone fasteners includes advancing one of the bone fasteners at an angle into a position subjacent an articular surface of the long bone.

4. A method of claim 1, further comprising attaching a targeting guide to the guide frame with a positive fit, said targeting guide defining at least one guide opening, and advancing one of the bone fasteners through the guide opening, the long bone and into the one of the openings defined in the fixation member.

5. A method of claim 4, further comprising extending a temporary fastener through a temporary fastener opening defined in the targeting guide so as to temporarily secure the guide frame prior to advancing the bone fasteners.

6. A method of claim 4, wherein attaching the targeting guide comprises slidably engaging the targeting guide with the guide frame.

7. A method of claim 1, further comprising inserting a broach having a size and shape similar to the fixation member through the side aperture and into the medullary canal prior to inserting the fixation member.

8. A method of claim 1, wherein advancing bone fasteners include advancing all of the bone fasteners for the procedure with the guide frame.

9. The method of claim 1, further comprising attaching a handle to the guide attachment member prior to inserting the fixation member through the side aperture.

10. The method of claim 9, further comprising detaching the handle from the guide attachment member after inserting the fixation member in the medullary canal and side aperture.

11. A method of claim 1, wherein extending a guide attachment fastener comprises threading the guide attachment fastener into a threaded opening defined in the exposed end of the fixation member.

12. A method of repairing a fractured long bone, wherein the long bone includes a medullary canal, said method comprising:
defining a side aperture in the long bone subjacent cartilage and near an end of the long bone, said side aperture extending into the medullary canal of the long bone;
providing a fixation member sized for insertion into the medullary canal of the long bone, the fixation member defining at least one opening sized for passage of bone fasteners into the fixation member;
providing a guide assembly comprising a guide frame having a first end and a second end, the guide frame defining at least one fastener guide opening therethrough proximal to the first end; a guide attachment member extending from the guide frame proximal to the first end thereof and defining an opening therethrough, wherein the guide attachment member is configured for forming a positive fit between the guide attachment member and a mating surface of the fixation member, wherein the guide attachment member defines one or more prongs adapted for forming a positive fit with the mating surface of the fixation member;
attaching the guide attachment member to the fixation member such that the guide attachment member achieves a positive fit with the fixation member;
inserting a guide attachment fastener through the opening of the guide attachment member and securing the guide attachment fastener to the fixation member;
inserting the fixation member through the side aperture until the fixation member is positioned in the medullary canal with the guide assembly attached thereto; and
advancing a bone fastener through each of said at least one fastener guide openings defined in the guide frame, through the long bone, and into said at least one opening defined in the fixation member, wherein advancing comprising advancing a bone fastener through a guide opening defined in the guide attachment fastener.

13. The method of claim 12, further comprising attaching a targeting guide to the guide frame proximal to the second end of the guide frame, said targeting guide defining at least one fastener guide opening, and advancing a bone fastener through each of said fastener guide openings, through the long bone, and into an opening defined in the fixation member.

14. A method of claim 13, further comprising extending a temporary fastener through a temporary fastener opening defined in the targeting guide so as to temporarily secure the guide frame prior to advancing the bone fastener.

15. A method of claim 13, wherein attaching the targeting guide comprises slidably engaging the targeting guide with the guide frame.

16. A method of claim 12, further comprising extending a screw guide into each of the at least one fastener guide openings defined in the guide frame, wherein advancing a bone fastener includes advancing the bone fastener through an opening defined in the screw guide.

17. A method of claim 12, wherein advancing the bone fastener includes advancing the bone fastener at an angle into a position subjacent an articular surface of the long bone.

18. A method of claim 12, further comprising inserting a broach having a size and shape similar to the fixation member through the side aperture and into the medullary canal prior to inserting the fixation member.

19. A method of claim 12, wherein advancing a bone fastener includes advancing all of the bone fasteners for the procedure with the guide frame.

20. A method of claim 12, wherein extending a guide attachment fastener comprises threading the guide attachment fastener into a threaded opening defined in the exposed end of the fixation member.

21. A method of claim 12, further comprising attaching a handle to the guide attachment member prior to inserting the fixation member through the side aperture.

22. A method of claim 21, further comprising detaching the handle from the guide attachment member after inserting the fixation member in the medullary canal and side aperture.

23. A method of repairing a fractured long bone, wherein the long bone includes a medullary canal, said method comprising:
defining a side aperture in the long bone subjacent cartilage and near an end of the long bone, said side aperture extending into the medullary canal of the long bone;
providing a fixation member sized for insertion into the medullary canal of the long bone, the fixation member defining at least one opening sized for passage of bone fasteners into the fixation member;
providing a guide assembly comprising a guide frame having a first end and a second end, the guide frame defining at least one fastener guide opening therethrough proximal to the first end; a guide attachment member extending from the guide frame proximal to the first end thereof and defining an opening therethrough, wherein the guide attachment member is configured for forming a positive fit between the guide attachment member and a mating surface of the fixation member, wherein the guide attachment member defines a plurality of prongs or indentations adapted for forming a positive fit with the mating surface of the fixation member, wherein the plurality of prongs or indentations are spaced around the circumference of the opening in the guide attachment member;
attaching the guide attachment member to the fixation member such that the guide attachment member achieves a positive fit with the fixation member;
inserting a guide attachment fastener through the opening of the guide attachment member and securing the guide attachment fastener to the fixation member;
inserting the fixation member through the side aperture until the fixation member is positioned in the medullary canal with the guide assembly attached thereto; and
advancing a bone fastener through each of said at least one fastener guide openings defined in the guide frame, through the long bone, and into said at least one opening defined in the fixation member, wherein advancing comprises advancing a bone fastener through a guide opening defined in the guide attachment fastener.

24. The method of claim 23, further comprising attaching a targeting guide to the guide frame proximal to the second end of the guide frame, said targeting guide defining at least one fastener guide opening, and advancing a bone fastener through each of said fastener guide openings, through the long bone, and into an opening defined in the fixation member.

25. A method of claim 24, further comprising extending a temporary fastener through a temporary fastener opening defined in the targeting guide so as to temporarily secure the guide frame prior to advancing the bone fastener.

26. A method of claim 24, wherein attaching the targeting guide comprises slidably engaging the targeting guide with the guide frame.

27. A method of claim 23, further comprising extending a screw guide into each of the at least one fastener guide openings defined in the guide frame, wherein advancing a bone fastener includes advancing the bone fastener through an opening defined in the screw guide.

28. A method of claim 23, wherein advancing the bone fastener includes advancing the bone fastener at an angle into a position subjacent an articular surface of the long bone.

29. A method of claim 23, further comprising inserting a broach having a size and shape similar to the fixation member through the side aperture and into the medullary canal prior to inserting the fixation member.

30. A method of claim 23, wherein advancing the bone fastener includes advancing all of the bone fasteners for the procedure with the guide frame.

31. A method of claim 23, wherein extending a guide attachment fastener comprises threading the guide attachment fastener into a threaded opening defined in the exposed end of the fixation member.

32. A method of claim 23, further comprising attaching a handle to the guide attachment member prior to inserting the fixation member through the side aperture.

33. A method of claim 32, further comprising detaching the handle from the guide attachment member after inserting the fixation member in the medullary canal and side aperture.

34. A method of repairing a fractured long bone, wherein the long bone includes a medullary canal, said method comprising:
    defining a side aperture in the long bone subjacent cartilage and near an end of the long bone, said side aperture extending into the medullary canal of the long bone;
    providing a fixation member sized for insertion into the medullary canal of the long bone, the fixation member defining at least one opening sized for passage of bone fasteners into the fixation member;
    providing a guide assembly comprising a guide frame having a first end and a second end, the guide frame defining at least one fastener guide opening therethrough proximal to the first end; a guide attachment member extending from the guide frame proximal to the first end thereof and defining an opening therethrough, wherein the guide attachment member is configured for forming a positive fit between the guide attachment member and a mating surface of the fixation member, wherein the guide attachment member defines a plurality of prongs or indentations adapted for forming a positive fit with the mating surface of the fixation member, wherein the plurality of prongs or indentations are spaced around the circumference of the opening in the guide attachment member;
    attaching the guide attachment member to the fixation member such that the guide attachment member achieves a positive fit with the fixation member;
    inserting a guide attachment fastener through the opening of the guide attachment member and securing the guide attachment fastener to the fixation member;
    attaching a handle to the guide attachment member prior to insertion of the fixation member;
    inserting the fixation member through the side aperture until the fixation member is positioned in the medullary canal with the guide assembly attached thereto;
    detaching the handle from the guide attachment member after inserting the fixation member in the medullary canal and side aperture; and
    advancing a bone fastener through each of said at least one fastener guide openings defined in the guide frame, through the long bone, and into said at least one opening defined in the fixation member.

35. A method of claim 34, further comprising extending a screw guide into each of the at least one fastener guide openings defined in the guide frame, wherein advancing a bone fastener includes advancing the bone fastener through an opening defined in the screw guide.

36. A method of claim 34, wherein advancing the bone fastener includes advancing the bone fastener at an angle into a position subjacent an articular surface of the long bone.

37. A method of claim 34, further comprising attaching a targeting guide to the guide frame proximal to the second end of the guide frame, said targeting guide defining at least one fastener guide opening, and advancing a bone fastener through each of said fastener guide openings, through the long bone, and into an opening defined in the fixation member.

38. A method of claim 37, further comprising extending a temporary fastener through a temporary fastener opening defined in the targeting guide so as to temporarily secure the guide frame prior to advancing the bone fasteners.

39. A method of claim 37, wherein attaching the targeting guide comprises slidably engaging the targeting guide with the guide frame.

40. A method of claim 34, further comprising inserting a broach having a size and shape similar to the fixation member through the side aperture and into the medullary canal prior to inserting the fixation member.

41. A method of claim 34, wherein advancing the bone fastener includes advancing all of the bone fasteners for the procedure with the guide frame.

42. A method of claim 34, wherein extending a guide attachment fastener comprises threading the guide attachment fastener into a threaded opening defined in the exposed end of the fixation member.

* * * * *

UNITED STATES PATENT AND TRADEMARK OFFICE
CERTIFICATE OF CORRECTION

PATENT NO. : 7,588,577 B2  Page 1 of 1
APPLICATION NO. : 10/891738
DATED : September 15, 2009
INVENTOR(S) : Fencl et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1406 days.

Signed and Sealed this

Twenty-first Day of September, 2010

David J. Kappos
*Director of the United States Patent and Trademark Office*